US011133087B2

(12) United States Patent
Humphrey

(10) Patent No.: US 11,133,087 B2
(45) Date of Patent: Sep. 28, 2021

(54) ADAPTIVE LANE DETECTION SYSTEMS AND METHODS

(71) Applicant: LI-COR, Inc., Lincoln, NE (US)

(72) Inventor: Patrick G. Humphrey, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

(21) Appl. No.: 16/911,898

(22) Filed: Jun. 25, 2020

(65) Prior Publication Data

US 2021/0005290 A1 Jan. 7, 2021

Related U.S. Application Data

(60) Provisional application No. 62/869,361, filed on Jul. 1, 2019.

(51) Int. Cl.
  *G16H 10/40* (2018.01)
  *G06K 9/32* (2006.01)
  (Continued)

(52) U.S. Cl.
  CPC .......... *G16H 10/40* (2018.01); *G06K 9/3233* (2013.01); *G06T 7/0012* (2013.01); *G16H 30/40* (2018.01); *G06T 2207/10072* (2013.01)

(58) Field of Classification Search
  CPC ........ G06T 7/0012; G06T 2207/10072; G16H 10/40; G16H 30/40; G06K 9/3233
  See application file for complete search history.

(56) References Cited

U.S. PATENT DOCUMENTS 4,894,786 A * 1/1990 Hara ................ G01N 27/44717
  250/583
4,939,667 A * 7/1990 Hara ................ G01N 27/44717
  250/303
(Continued)

FOREIGN PATENT DOCUMENTS

CN  106558041 A  4/2017

OTHER PUBLICATIONS

Moreira et al., "Automatic Lane Segmentation in TLC Images Using the Continuous Wavelet Transform", Computational and Mathematical Methods in Medicine, vol. 2013, Article ID 218415, pp. 1-19 (Year: 2013).*

(Continued)

*Primary Examiner* — Nay A Maung
*Assistant Examiner* — Jose M Torres
(74) *Attorney, Agent, or Firm* — Leydig, Voit & Mayer, Ltd.; Gerald T. Gray

(57) ABSTRACT

Systems and methods for automatically identifying and characterizing one or more lanes in image data for one or more electrophoresed samples. The method includes receiving data representing an image of one or more electrophoresed samples, segmenting the data into one or multiple data segments or portions within a region of interest (ROI), wherein the one or multiple data segments represent (e.g., when visually displayed) one or multiple lane segments along a first axis in the ROI, each of the one or multiple lane segments traversing one or multiple lanes in the image data, generating an intensity profile for at least a first data segment of the one or multiple data segments along a second axis orthogonal to the first axis, and processing the intensity profile to determine a location and parameters for each of one or multiple lanes in the first data segment.

22 Claims, 25 Drawing Sheets

(51) Int. Cl.
*G16H 30/40* (2018.01)
*G06T 7/00* (2017.01)

(56) References Cited

U.S. PATENT DOCUMENTS

| | | | |
|---|---|---|---|
| 5,297,288 A * | 3/1994 | Hemminger | G01N 21/5911 |
| | | | 382/129 |
| 9,230,185 B1 * | 1/2016 | Berry | G06K 9/36 |
| 2003/0143554 A1 | 7/2003 | Berres et al. | |
| 2006/0058969 A1 * | 3/2006 | Liao | G16B 30/00 |
| | | | 702/20 |
| 2006/0257053 A1 | 11/2006 | Boudreau et al. | |
| 2014/0106989 A1 | 4/2014 | Barich et al. | |
| 2018/0209935 A1 | 7/2018 | Nishida | |
| 2020/0319140 A1 * | 10/2020 | Saratkar | G06K 9/00147 |

OTHER PUBLICATIONS

Lin et al., "Automatic Method to Compare the Lanes in Gel Electrophoresis Images", IEEE Transactions on Information Technology in Biomedicine, vol. 11, No. 2, Mar. 2007, pp. 179-189 (Year: 2007).*
Written Opinion of the International Search Authority, dated Oct. 13, 2020 in Application No. PCT/US2020/040249.
International Search Report of the International Search Authority, dated Oct. 13, 2020 in Application No. PCT/US2020/040249.

* cited by examiner

ADAPTIVE LANE DETECTION SYSTEMS AND METHODS

CROSS-REFERENCE TO RELATED APPLICATION

This application claims the benefit of priority to U.S. Provisional Patent Application No. 62/869,361, filed Jul. 1, 2019, which is hereby incorporated by reference in its entirety.

BACKGROUND

The present disclosure provides systems and methods for automatically detecting lanes on images of electrophoresed samples.

When analyzing electrophoresed samples on a gel, on a membrane following Western Blot analysis or on a substrate, for example, one of the first steps is to identify the lanes (the number, location and orientation) in an image generated after electrophoresis and/or followed by electrophoresed sample transfer to a membrane or other substrate. Oftentimes the lane widths vary from lane to lane. Also, the width of each individual lane can vary from the top to the bottom of the gel, membrane or substrate. Additionally, the lanes do not always run straight, nor do they always run parallel to each other. Moreover, the lanes are not always evenly spaced nor are the lane signal intensities uniform. These anomalies are the results of the biology, chemistry and physics when electrophoresing samples and vary from gel to gel, membrane to membrane or substrate to substrate as well as within each individual gel, membrane or substrate. This can be problematic when attempting to perform an accurate analysis of the electrophoresed samples. Present manual and automated techniques for analyzing electrophoresis data are tedious, error-prone, and unreliable.

SUMMARY

The adaptive lane detection systems and methods according to the present embodiments automatically and accurately detect the number of lanes as well as the left and right boundaries of each corresponding lane in an image of electrophoresed samples. The embodiments are also able to account for variable lane widths, non-uniform signal intensities, and varying degrees of lane curvature. The embodiments advantageously solve the challenging problem of detecting and extracting the lane boundary characteristics on an image of electrophoresed samples where the lane characteristics may be inconsistent and are often located on a non-uniform background which can contain other gel, membrane or substrate artifacts.

According to an embodiment, a computer-implemented method of automatically identifying and characterizing one or more lanes in image data for one or more electrophoresed samples is provided. The method includes receiving data representing an image of one or more electrophoresed samples, segmenting the data into one or multiple data segments or portions within a region of interest (ROI), wherein the one or multiple data segments represent (e.g., when visually displayed) one or multiple lane segments along a first axis in the ROI, each of the one or multiple lane segments traversing one or multiple lanes of the one or more lanes in the image data, generating an intensity profile for at least a first data segment of the one or multiple data segments along a second axis orthogonal to the first axis (e.g., by summing up intensity values along the second axis for each first axis location), processing the intensity profile to determine a location and parameters for each of one or multiple lanes in the first data segment, and outputting the determined locations and parameters of the one or multiple lanes in the first data segment. It should be understood that a "data segment" may also be referred to herein as a "ROI segment".

In certain aspects, the method further includes rendering an image of the one or multiple lanes in the first data segment in the ROI, and/or an outline of the one or multiple lanes in the first data segment in the ROI based on the determined locations and parameters of the one or multiple lanes in the first data segment. In certain aspects, generating the intensity profile includes summing up intensity values in the first data segment along the second axis for each of a plurality of first axis locations.

According to an embodiment, a computer-implemented method of automatically identifying and characterizing one or more lanes in image data for one or more electrophoresed samples is provided. The method includes receiving data representing an image of one or more lanes of electrophoresed samples, segmenting the data into one or multiple data segments within a region of interest (ROI), wherein the one or multiple data segments represent one or multiple lane segments along a first axis in the ROI, each of the one or multiple lane segments traversing multiple lanes of the one or more lanes in the image data, generating an intensity profile for at least a first data segment of the one or multiple data segments along a second axis orthogonal to the first axis in the ROI, processing the intensity profile to determine a location and parameters for each of one or multiple lanes in the first data segment, and outputting the determined locations and parameters of the one or multiple lanes in the first data segment.

In certain aspects, the method further includes, for each of the one or multiple lanes in the one or multiple data segments, rendering an image of the one or multiple lanes and/or an outline of the one or multiple lanes in the one or multiple data segments based on the determined locations and parameters of the one or multiple lanes in the one or multiple data segments. In certain aspects, the method further include, for each of the one or multiple lanes, combining together the corresponding locations and parameters determined for each of the one or multiple data segments.

According to certain aspects, a method may further include receiving a selection of the ROI, the ROI including data representing the one or multiple lanes. In certain aspects, the selection of the ROI includes a selection received from a user input device. In certain aspects, the selection of the ROI includes a selection received from, or identified by, an artificial intelligence algorithm.

According to certain aspects, the parameters may include an approximate lane width value, and the processing includes determining the approximate lane width value for the one or multiple lanes. In certain aspects, determining the approximate lane width value includes: calculating a derivative of the intensity profile across the first axis to produce a differential curve, the differential curve including positive and negative differential curve pairs; iteratively producing an array of shifted differential curves by: incrementally shifting the positive and negative differential curve pairs relative to each other by incremental amounts defined by a minimum and a maximum lane width shift parameter value; and combining the positive and negative differential curve pairs together for each lane width shift parameter value to produce a shifted differential curve; for each of the shifted differential curves in the array: squaring or taking the absolute value and combining the differential curve, and determining a lane width fit error; and determining a minimum lane width fit error, wherein the lane width shift parameter value corresponding to the minimum lane width fit error is determined as the approximate lane width value.

In certain aspects, a method may further include detecting the one or multiple lanes in the one or multiple data segments based on the determined approximate lane width value.

In certain aspects, detecting the one or multiple lanes in a data segment includes: determining a minimum lane width value, a maximum lane width value and an increment value based on the approximate lane width value; and detecting an optimal lane width and locations for each of the one or more lanes using an iterative lane width and location determination algorithm, wherein for each incremental value starting with the maximum or minimum lane width value, a model profile is determined and compared with the intensity profile in the one or multiple data segments.

According to an embodiment, a system is provided that is configured to automatically identify and characterize one or more lanes in image data for one or more electrophoresed samples, the system comprising one or more processors, and a memory storing instructions, which when executed by the one or more processors, cause the one or more processors to receive or acquire data representing an image of one or more lanes of electrophoresed samples, segment the image into one or multiple data segments within a region of interest (ROI), along a first axis in the ROI, each of the one or multiple data segments traversing one or multiple lanes of the one or more lanes, generate an intensity profile for at least a first data segment of the one or multiple data segments along a second axis orthogonal to the first axis in the ROI, process the intensity profile to determine a location and parameters for each of the one or multiple lanes in the first data segment, and output the determined locations and parameters of the one or multiple lanes in the first data segment.

According to a further embodiment, a system is provided that is configured to automatically identify and characterize one or more lanes in image data for one or more electrophoresed samples, the system comprising one or more processors, and a memory storing instructions, which when executed by the one or more processors, cause the one or more processors to receive data representing an image of one or more electrophoresed samples, segment the image data into one or multiple data segments within a region of interest (ROI) along a first axis in the ROI, each of the one or multiple data segments traversing one or multiple lanes, generate an intensity profile for each of the one or multiple data segments along a second axis orthogonal to the first axis in the ROI, process each intensity profile to determine a location and parameters for each corresponding segment of the one or multiple data segments, and output the determined locations and parameters of the one or multiple lanes for each of the one or multiple data segments.

In a further embodiment, a non-transitory computer readable medium is provided that stores instructions, which when executed by one or more processors, cause the one or more processors to implement a method of automatically identifying and characterizing one or more lanes in image data for one or more electrophoresed samples as described herein.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Accurate quantitative analysis of image data derived from electrophoresis or Western Blot analysis is dependent upon the accurate characterization of the locations of the lanes. The adaptive lane detection systems and methods of the present embodiments automatically and accurately detect and characterize the number of lanes as well as the left and right boundaries of each corresponding lane in an image of electrophoresed samples. The embodiments are also able to account for variable lane widths, non-uniform signal intensities, and varying degrees of lane curvature. The embodiments advantageously solve the challenging problem of detecting and extracting the lane boundary characteristics on an image of electrophoresed samples where the lane characteristics may be inconsistent and are often located on a non-uniform background which can contain other gel, membrane or substrate artifacts.

In one example, a region of interest (ROI) is specified and includes the desired lanes to be identified and characterized. In an x-y coordinate system, the lanes to be identified may run parallel to the y-axis and orthogonal to the x-axis. The region of interest is then divided along the y-axis into one or multiple sub-regions (or segments) extending along the x-axis. Each segment is then processed to determine a segment intensity profile along the y-axis, wherein each segment profile represents the cross-section of the intensity of the lanes along the x-axis of the ROI. Each segment profile is then processed by an iterative method to identify the left and right boundaries of each of the lanes within each of the segments in the ROI. The lane boundaries within a segment may be combined with corresponding lane boundaries from other segments to formulate the (entire) lane boundaries in the ROI.

Figure 1:
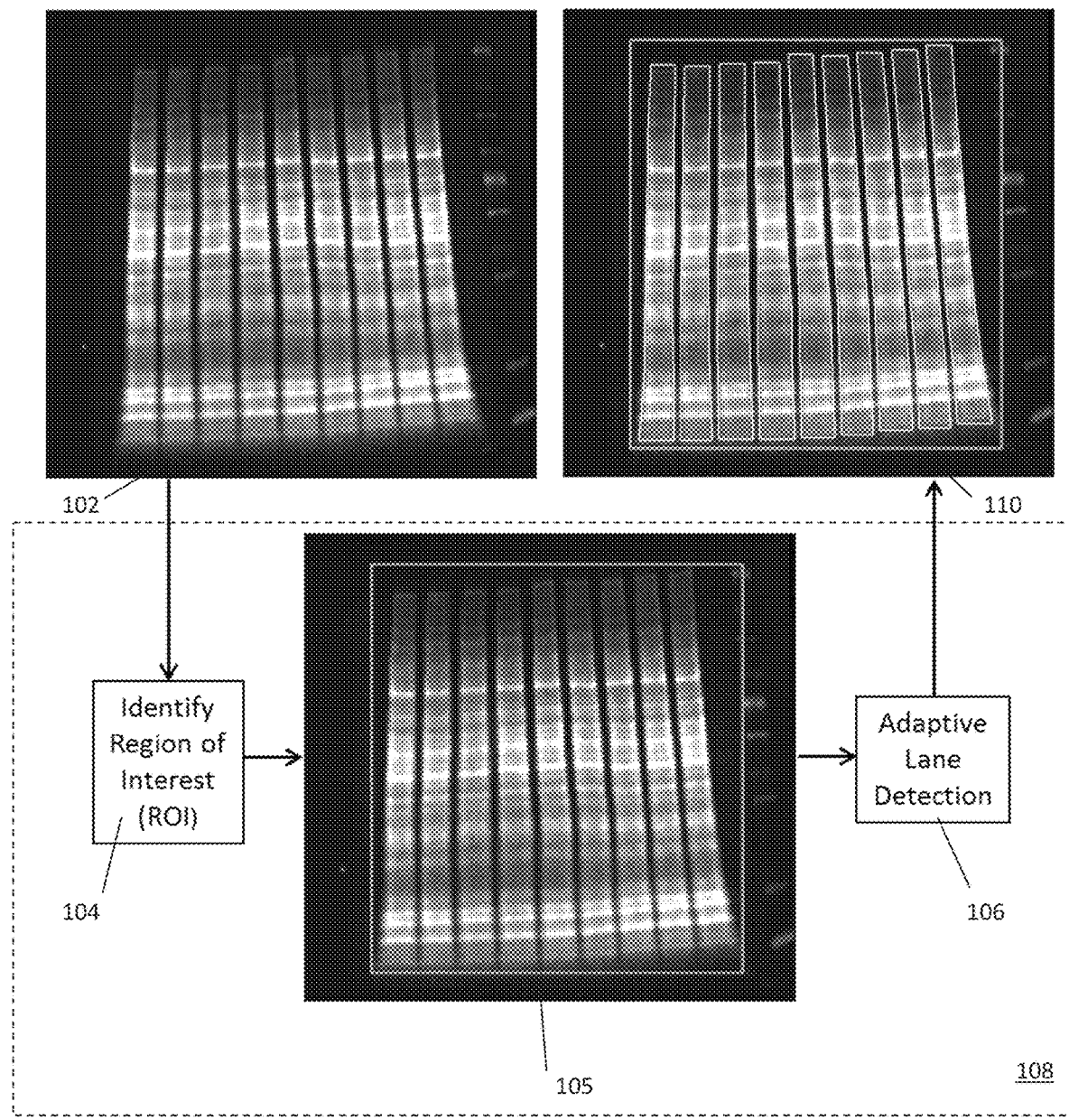
FIG. 1 is a conceptual diagram illustrating an adaptive lane detection system and general process flow, according to an example embodiment. Note that the lane boundaries have been identified in the output image.

FIG. 1 is a block diagram of an example process flow for determining characteristics or attributes of lanes in electrophoresis data or similar data, according to an embodiment. As shown, electrophoresis image data (hereinafter image data) representing an image 102 is received (see, also FIG. 3). The image data (the "image data" may also be referred to herein as the "image") may be input or received from any data generating device and typically includes data representing one or more signal lanes. Examples of data generating devices include imaging devices or other devices that generate image data including multiple lanes.

The image 102 is received by lane detection and characterization engine 108. In one example, a region of interest (ROI) is identified at 104. The ROI includes the desired lanes to be identified and characterized. For example, the ROI may include the entire image 102 or a portion of the image 102. As shown in FIG. 1, image 105 illustrates an image wherein the ROI encompasses all lanes visually perceptible from the image 102. In an x-y coordinate system, the lanes to be identified may run parallel to the y-axis and orthogonal to the x-axis. As described in greater detail herein, at 106, lane detection and characterization engine 108 analyzes the image 102 to determine and characterize the constituent lanes present in the ROI of the image 102. Determined information such as the number of constituent lanes present and lane characteristics such as location, left and right boundaries are used to provide an output such as providing data characterizing the constituent lanes and/or rendering an output image 110 which represents a visual representation of the image data signal and its constituent lanes. As shown in FIG. 1, for example, image 102 is determined by the lane detection and characterization engine 108 to have nine (9) constituent lanes, and a display 110 is rendered showing an outline or overlay of the nine constituent lanes including the determined boundaries, which represents the signal content of the image 102. According to various embodiments, the lane detection and characterization engine 108 may be implemented in hardware, software, and/or a combination of hardware and software. Further, lane detection and characterization engine 108 may be implemented in a single processing device or in different processing devices.

Figure 2:
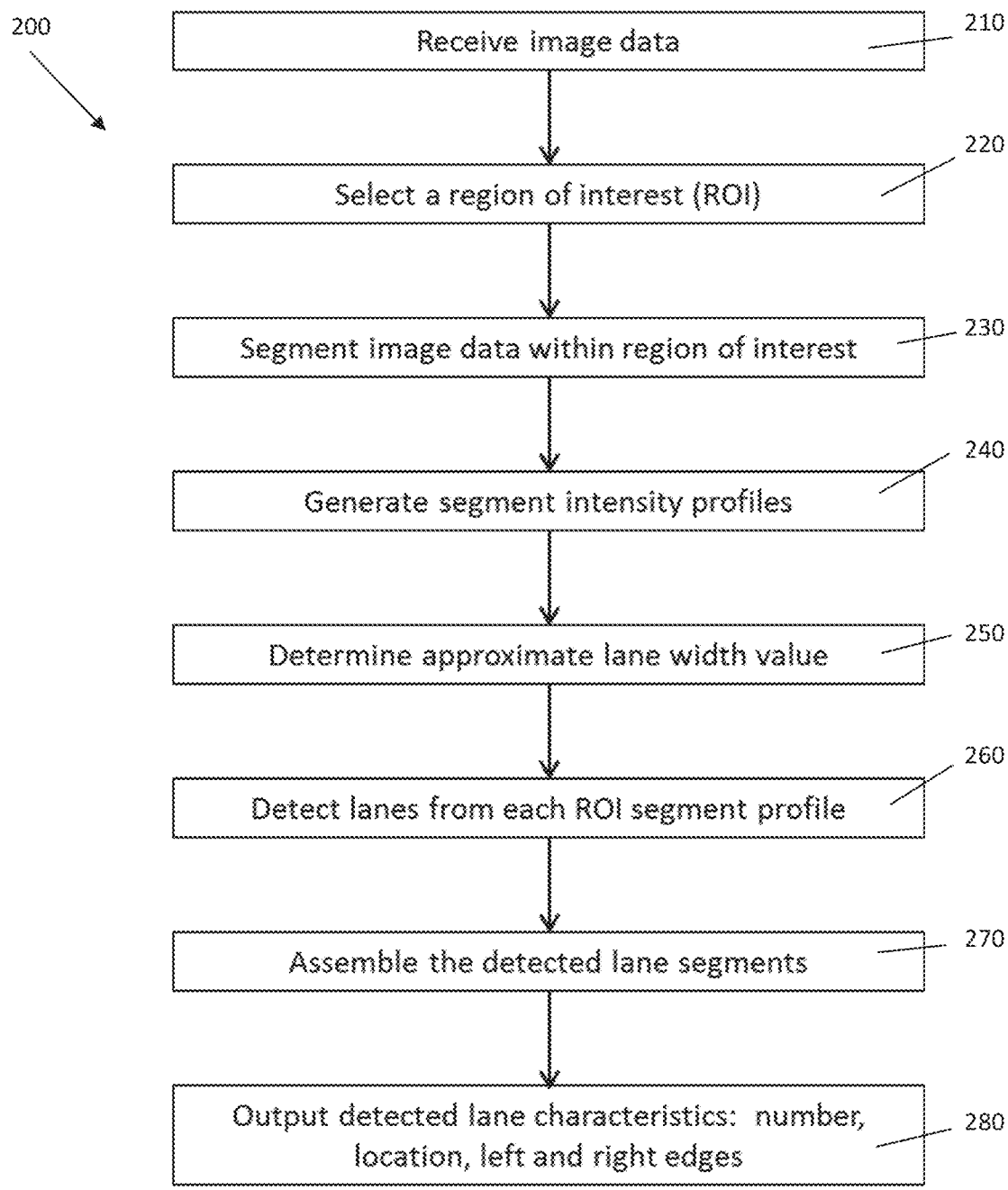
FIG. 2 is a flow diagram for a method for determining the lanes within image data, for a region of interest, according to an example embodiment.
Figure 3:
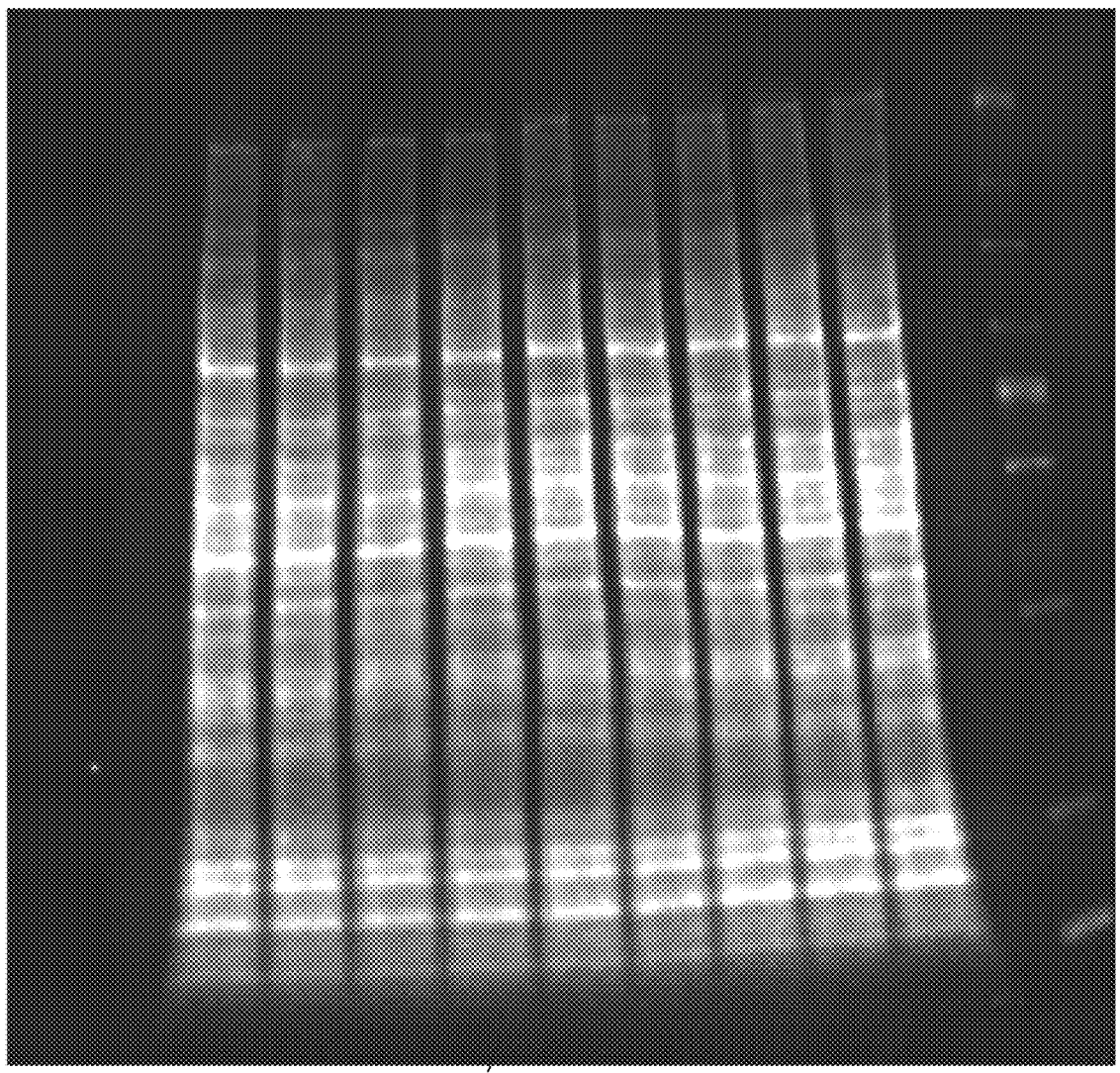
FIG. 3 illustrates an example of image data of electrophoresed samples. Image collected of a membrane following the performance of Western Blot analysis.

A flow diagram of a method 200 for determining characteristics (e.g., the number, location, orientation, left and right edges) of the lanes present in image data of electrophoresed samples is illustrated in FIG. 2. The method 200 begins at step 210 by lane detection and characterization engine 108 receiving or acquiring an image (e.g., image 102) to be processed. The image data for the image to be processed typically includes intensity values for each pixel of the image. FIG. 3 illustrates an example input electrophoresis image 102.

Figure 4:
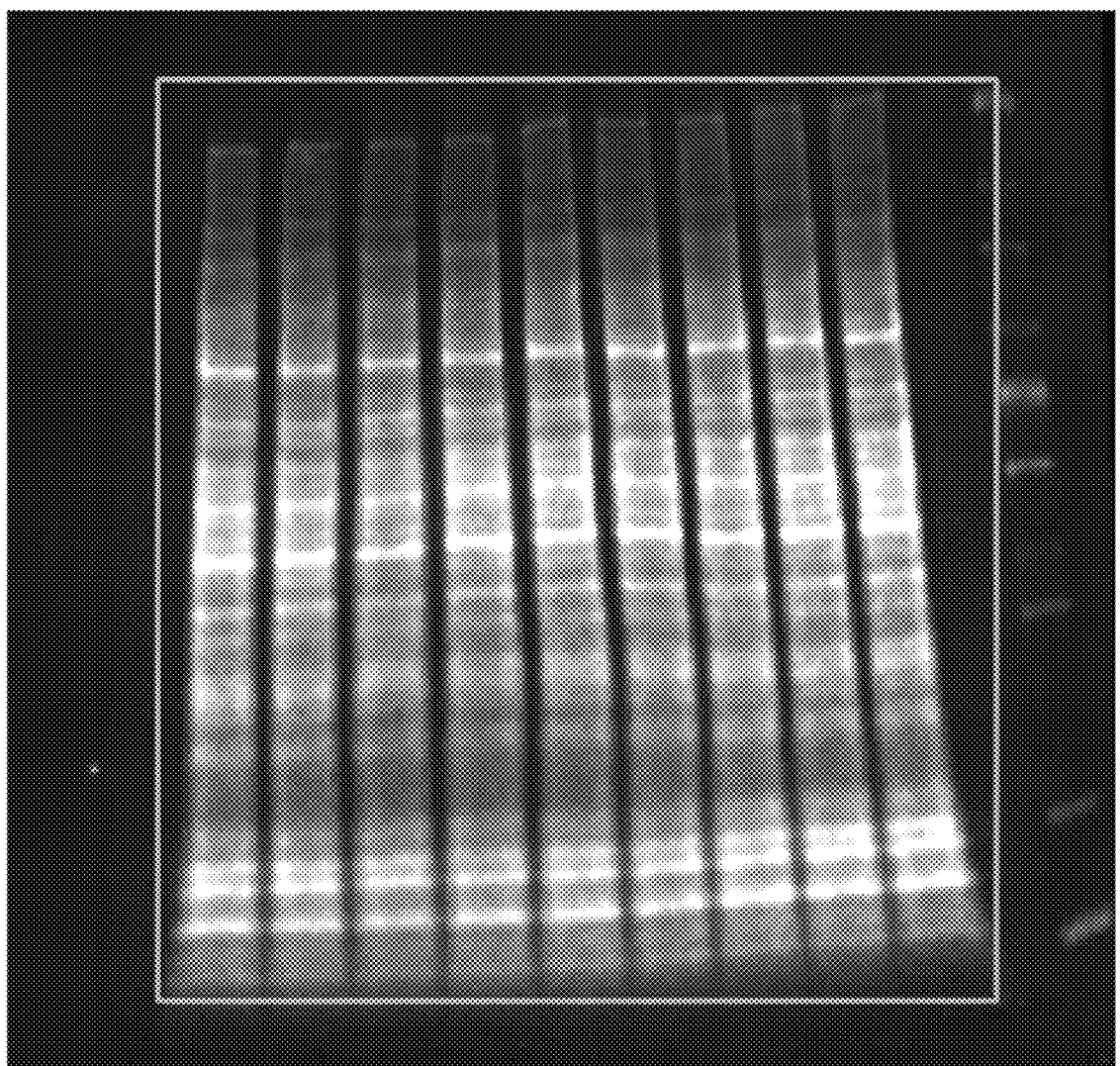
FIG. 4 illustrates an example of image data of electrophoresed samples region of interest (ROI).

At step 220, a region of interest (ROI) is identified or selected within the image 102. As shown in FIG. 4, the ROI may include substantially the entire image. In another embodiment, the ROI may include a portion of the entire image. In an embodiment, step 220 may include receiving a selection of the ROI from a user input device, e.g., user interface element that outlines or otherwise selects a defined portion of the image. In another embodiment, step 220 may include receiving a selection defined automatically, e.g., defined by an artificial intelligence (AI) algorithm configured to identify a ROI. The AI may include a neural network trained as appropriate for the image data received. An outline of the ROI may be rendered on the image as shown in FIG. 4.

Figure 5:
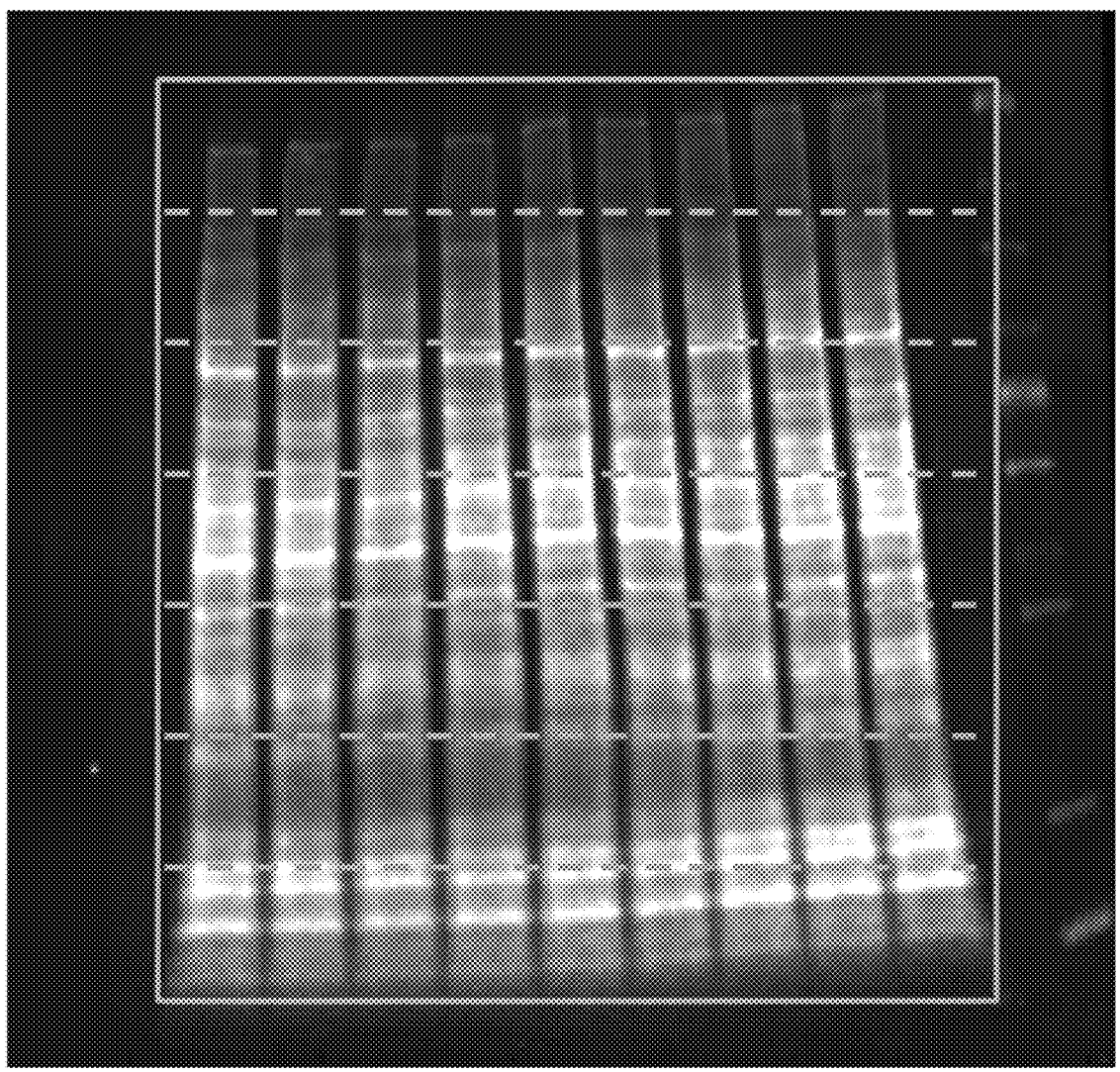
FIG. 5 illustrates an example of image data of electrophoresed samples region of interest (ROI) segments.

At step 230, the ROI is subdivided along the y-axis into one or multiple image sub-regions or segments. As shown in FIG. 5, an example of the defined ROI of FIG. 4 is subdivided into 7 segments. One skilled in the art will understand that the ROI may be subdivided into fewer or more segments, e.g., as few as one segment or as many segments as resolution along the y-axis will allow. As illustrated in FIG. 5, in an embodiment, each sub-region or segment spans the entire x-axis. In another embodiment, a segment may span only a portion of the x-axis, e.g., only spanning one or fewer than all lanes in the ROI.

Figure 6:
FIG. 6 illustrates an example of image data of electrophoresed samples region of interest (ROI) segment intensity profile.

At step 240, segment intensity profiles are generated for each of the subdivided regions/ROI segments, e.g., by summing along the y-axis within each of the segments. Each segment profile represents a cross-section of the lane intensity values along the x-axis for each of the ROI segments. An example segment intensity profile for one ROI segment from FIG. 5 is illustrated in FIG. 6.

Figure 7:
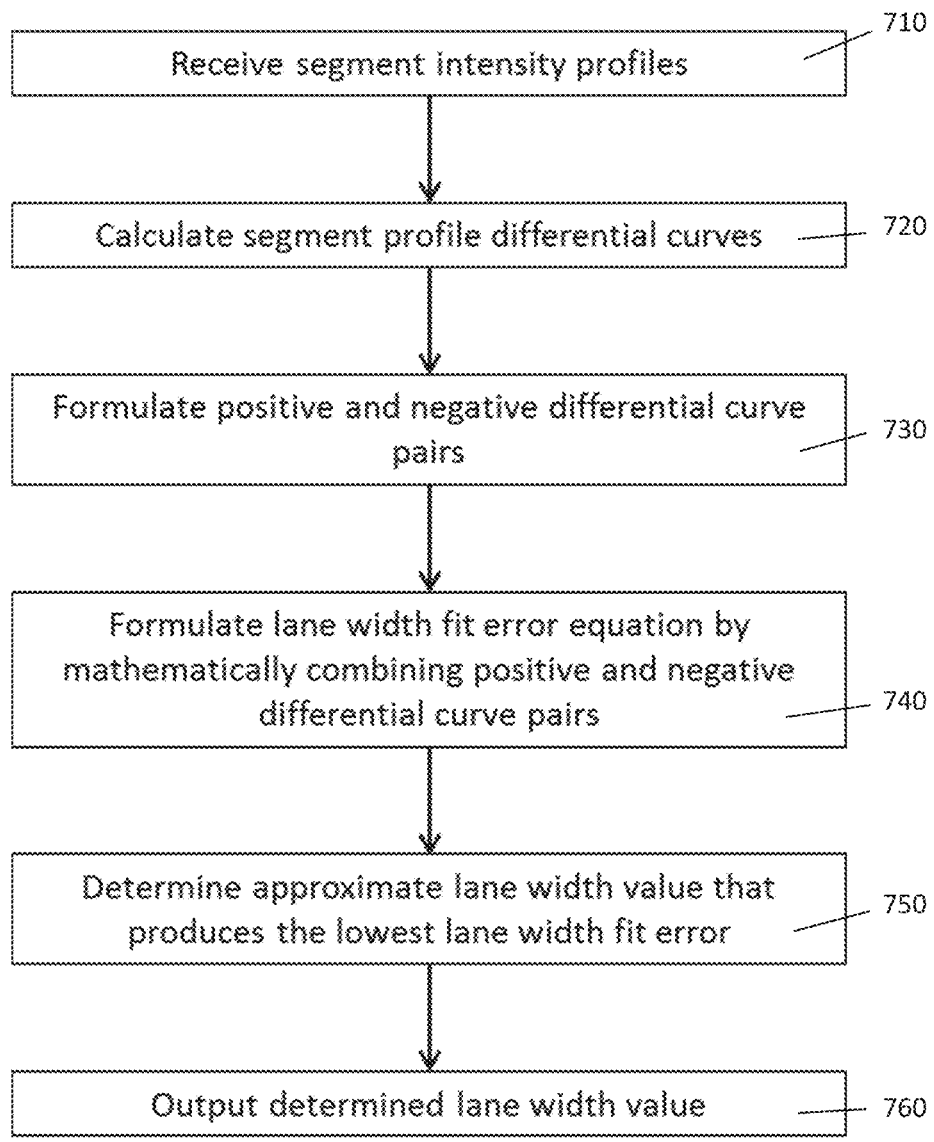
FIG. 7 shows a flow diagram for a method for determining the approximate lane width for image data of electrophoresed samples in the region of interest (ROI) segments, according to an example embodiment.

An approximate lane width value for each of the segment profiles is determined at step 250. A flow diagram illustrating an embodiment of a method for determining an approximate lane width value is shown in FIG. 7 (and discussed in more detail below). This is an important step in the characterization of individual lanes. When manually analyzing electrophoresed samples, one of the first things the user may do is formulate a visual approximation of the lane widths and/or widths of bands within the lanes. This enables the user to group the bands into their prospective lanes and to differentiate valid lanes from invalid artifacts. This also enables the lane detection algorithm to be more efficient and robust by targeting the lanes that have valid lane width characteristics.

At step 260, the lane(s) from each of the ROI segment intensity profiles being processed are identified or detected using the determined approximate lane width value(s) from step 250. A flow diagram illustrating an embodiment of a method for implementing step 260 will be discussed in more detail below with regard to FIG. 10.

At step 270, identified lane segments from each ROI segment may be assembled together, e.g., to form entire lanes. For example, based on x-axis locations, lanes segments having similar or overlapping locations may be combined to form full lanes in the image.

Figure 22:
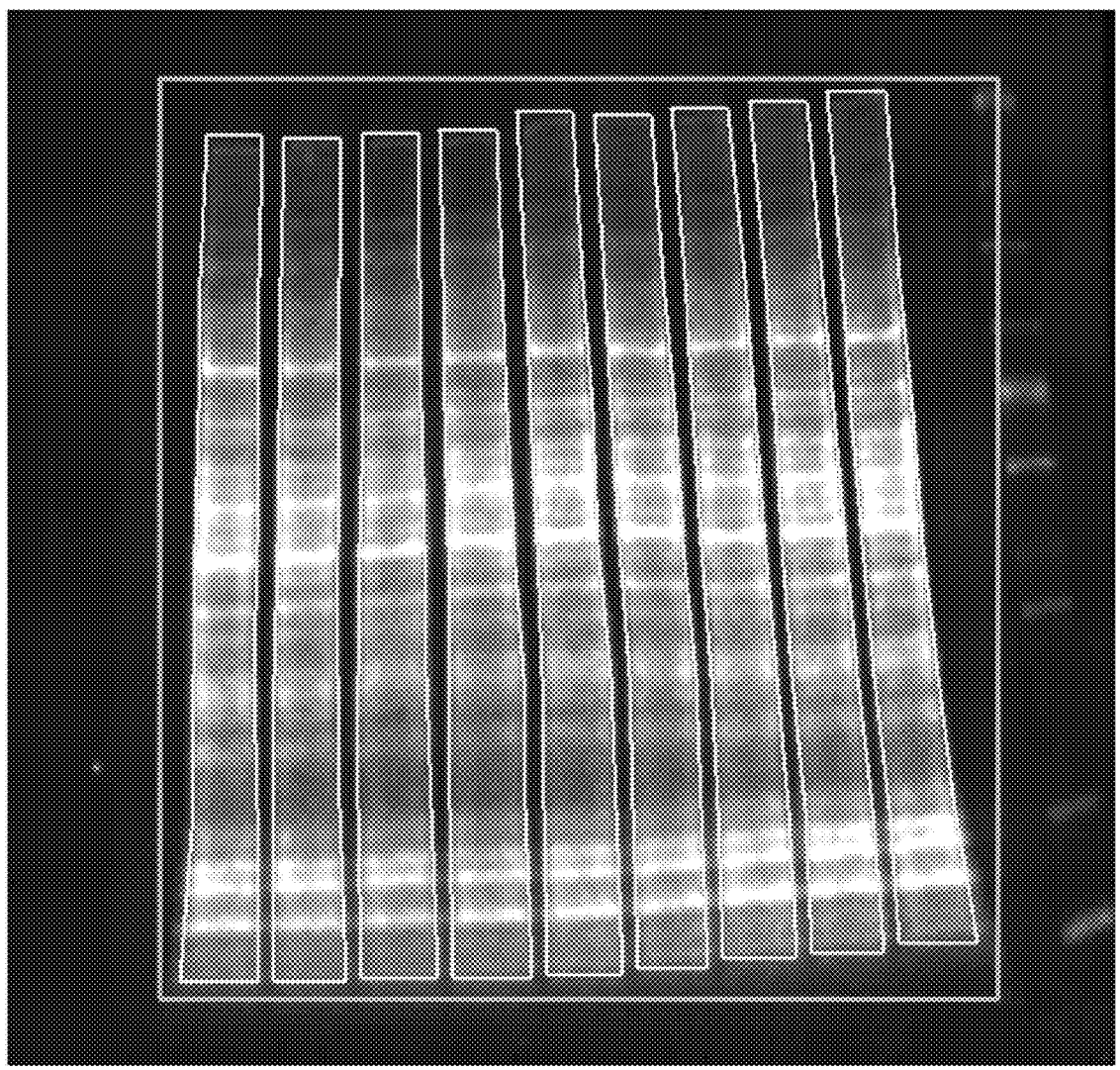
FIG. 22 is a conceptual diagram illustrating the detected lane results of the method for an example image ROI, according to an example embodiment.

At step 280, the detected lane characteristics or parameters are output. Output lane characteristics may include the number of lanes, the locations of lanes, the left and right edges of lanes, etc., and may be displayed as values, or output or stored for use by another processing algorithm or processing system. In an embodiment, an image of one or more lanes in each data segment and/or an outline of the one or more lanes in each data segment may be rendered based on the determined locations and parameters of the one or more lanes in each data segment. FIG. 22 shows an example of a rendering of the entire received image (e.g., image 102) including an outline of all lanes determined by the lane characterization engine 108.

It should be appreciated that various processing steps as described herein above and below may occur in series/sequentially, simultaneously/in parallel, or individually as would be apparent to one skilled in the art. For example, the determination of features such as the intensity profiles, lanes (location, widths, etc.), and fit error in one ROI segment can occur simultaneously/independent to the determination of the same features in the other ROI segments. As another example, multiple ROI segments may be processed sequentially or in parallel and/or within any segment, multiple lanes may be identified/processed sequentially or in parallel.

As illustrated in FIG. 7, according to an embodiment, an approximate lane width determination method (step 250) is initiated at step 710 by receiving the previously created segment profile(s) from step 240 for each of the ROI segments. At step 720, each of the profiles is converted to a differential curve, e.g., a segment profile differential curve is calculated for each received profile. In an embodiment, step 720 is implemented in accordance with Equation 1 as follows:

$$diff_{(i,j)} = \frac{n \sum_{k=0}^{n-1} (x_{(i,j+k)} \cdot y_{(i,j+k)}) - \sum_{k=0}^{n-1} x_{(i,j+k)} \cdot \sum_{k=0}^{n-1} y_{(i,j+k)}}{n \left( \sum_{k=0}^{n-1} x_{(i,j+k)}^2 \right) - \left( \sum_{k=0}^{n-1} x_{(i,j+k)} \right)^2} \quad (1)$$

where $x_{(i,j+k)}$=segment profile data point locations,
$y_{(i,j+k)}$=segment profile data point intensity values,
i=1 to M (M=number of segment profiles),
j=1 to P (P=number of differential segment profile data points),
P=N−n+1,
N=number of segment profile data points,
n=number of segment profile subsample data points, and
k=segment profile subsample index variable.

Figure 8:
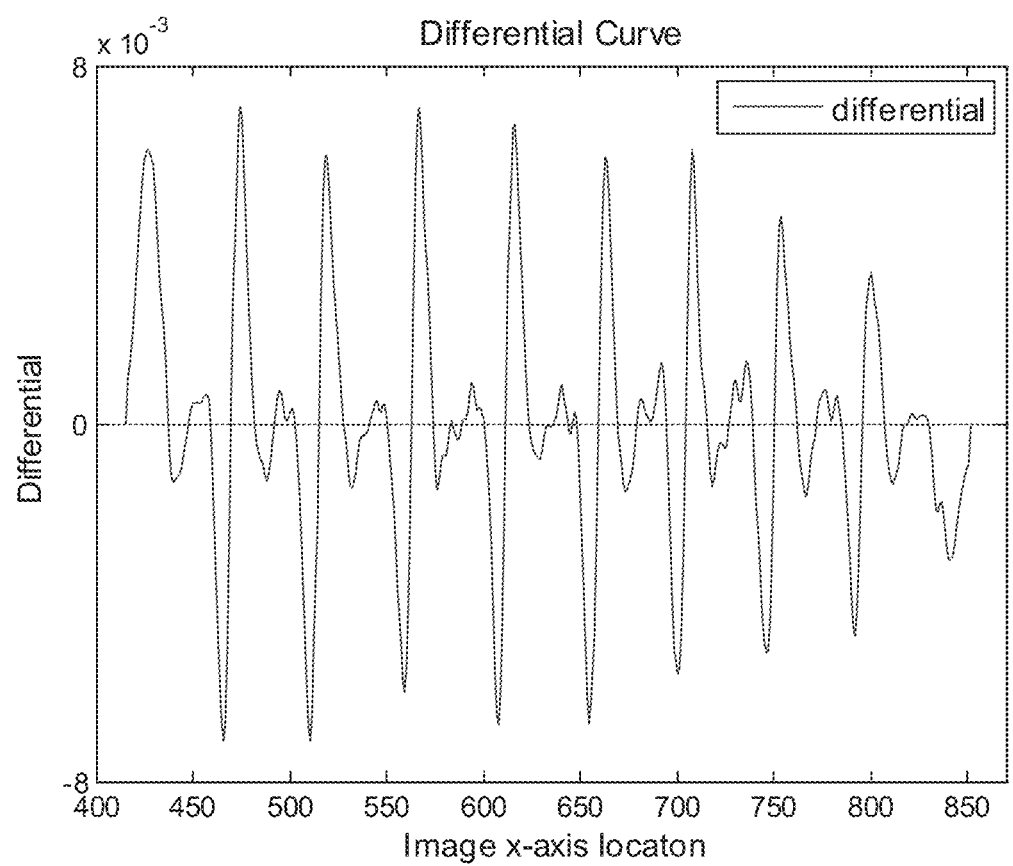
FIG. 8 shows a differential curve generated by calculating a differential of image data of electrophoresed samples region of interest (ROI) segment intensity profile, according to an example embodiment.

An example of a differential curve generated from Equation 1 is illustrated in FIG. 8. In an embodiment, at step 730, each differential curve is separated into positive and negative differential curve pairs. In an embodiment, a differential curve is separated in accordance with Equations 2 and 3 as follows:

$$posDiff_{(i,j)} = \begin{cases} diff_{(i,j)} & (diff_{(i,j)} > 0) \\ 0 & (diff_{(i,j)} \leq 0) \end{cases} \quad (2)$$

$$negDiff_{(i,j)} = \begin{cases} 0 & (diff_{(i,j)} \geq 0) \\ diff_{(i,j)} & (diff_{(i,j)} < 0) \end{cases} \quad (3)$$

In an embodiment, the positive and negative differential curve pairs are combined at step 740. In an embodiment, the positive and negative differential curve pairs are mathematically combined and a lane width fit error (lwFitErr$_w$) is formulated in accordance with Equation 4 for the determination of the approximate lane width value. Equation 4 is as follows:

$$lwFitErr_w = \left\{ \sum_{i=1}^{M} \left( \sum_{j=1+w}^{P} (posDiff_{(i,j-w)} + negDiff_{(i,j)})^2 + \sum_{j=P+1}^{P+w} (posDiff_{(i,j-w)} - negDiff_{(i,j-P)})^2 \right) \right\} \quad (4)$$

where
w=minimum to maximum lane width value.

Figure 9:
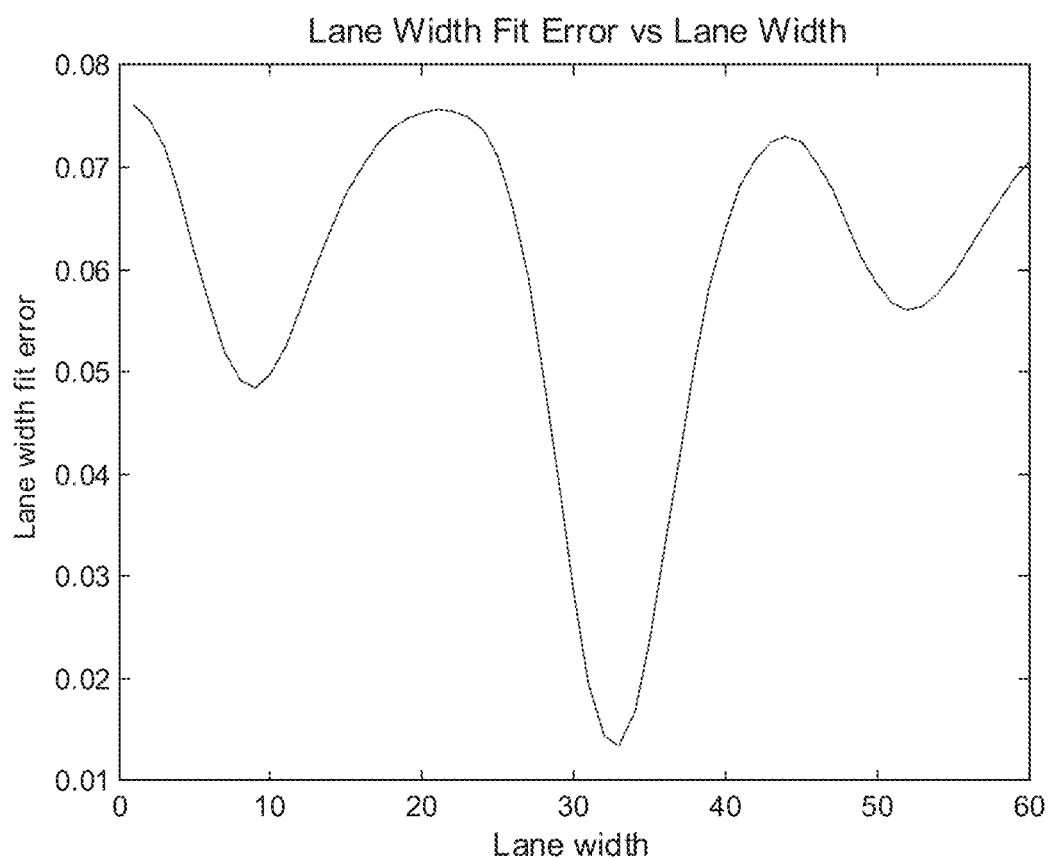
FIG. 9 illustrates a plot of Lane Width Fit Error vs Lane Width for image data of electrophoresed samples in the region of interest (ROI) segments, according to an example embodiment. Note that the minimum lane width fit error occurs at the approximate lane width value (33).

At step 750, an approximate lane width value that produces the lowest lane width fit error is determined. Adding the positive and negative differential curve pairs together results in the original calculated differential curve. In an embodiment, the positive and negative differential curves are incrementally shifted relative to each other and then added together to formulate an array of shifted differential curves. Each of these shifted differential curves may be squared (or the absolute value taken) and summed together, in which the resulting value can be utilized as an indicator of the approximate lane width. In an embodiment, the shift value resulting in the lowest sum of the squares represents the approximate lane width value. Equation 4 is a mathematical representation of an embodiment of the approximate lane width determination method, in which the sum of the squared differentials (or the absolute value) is calculated as a function of shift (lane width) and is illustrated in FIG. 9. It should be noted that the lane width fit error (lwFitErr$_w$) minimum value from Equation 4 occurs at the approximate lane width value, e.g., about 32 or 33 as shown in FIG. 9.

Figure 10:
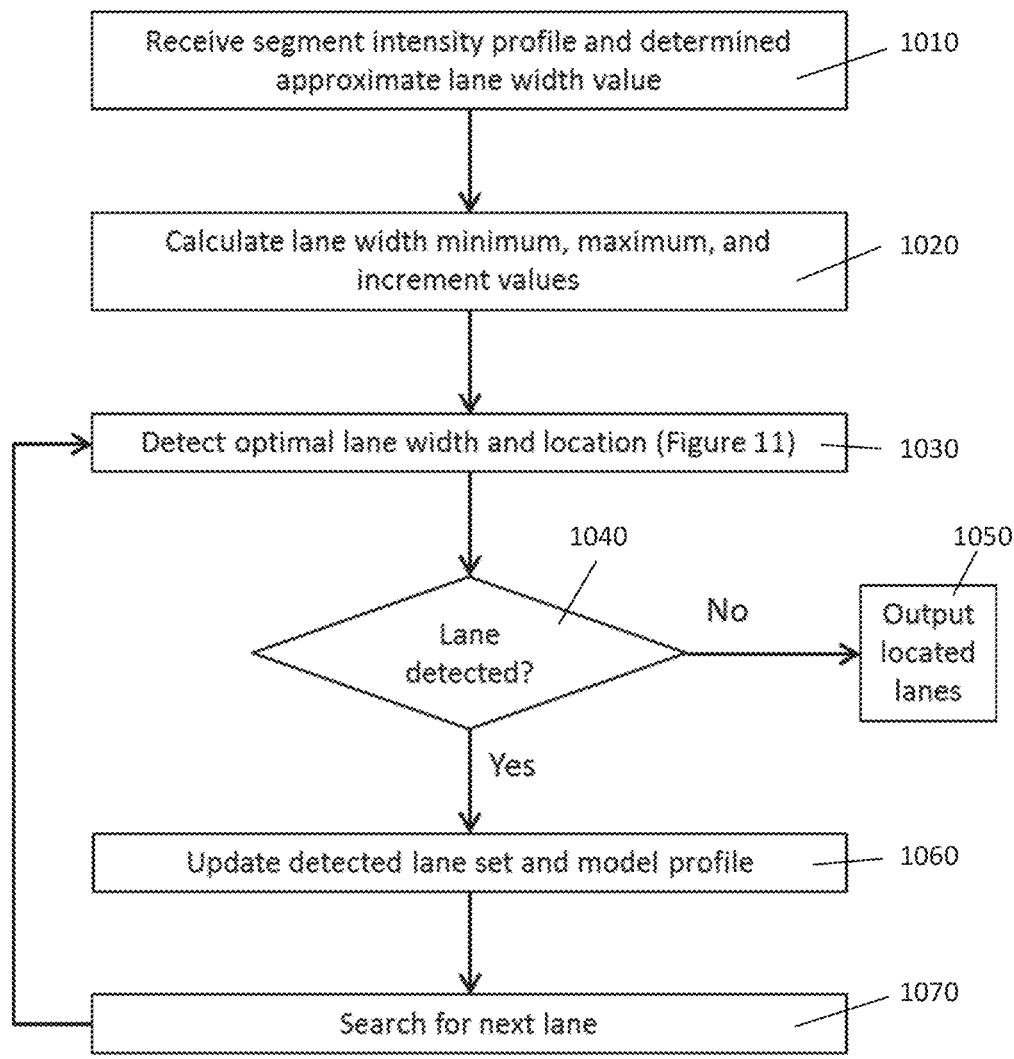
FIG. 10 is a flow diagram for a method for detecting lanes within an image ROI segment, according to an example embodiment.

At step 760, the determined approximate lane width value is output. The determined approximate lane width value may be utilized in the detection of the lanes for each ROI segment intensity profile at step 260. A flow diagram of a method for lane detection for each segment profile (step 260) is illustrated in FIG. 10. The method is initiated at step 1010 by receiving the segment intensity profile and the determined approximate lane width value. At step 1020, lane width minimum, maximum and incremental values are calculated. In an embodiment, the minimum, maximum and incremental lane width values may be calculated as a percentage of the pre-determined approximate lane width value.

At step 1030, locations and lane width values for each of the lanes in an ROI segment is determined by an iterative optimal lane width and location determination algorithm. An embodiment of a method for detecting an optimal lane width and location (step 1030) is illustrated in the flow diagram of FIG. 11 (discussed in more detail below). At decision step 1040, when a lane is detected, the process moves to step 1060 where the detected lane set and model profile is updated, e.g., data reflecting the detected lanes (lane set) and characteristics stored to a memory. Next, the process proceeds to step 1070 to search for another lane, returning to step 1030. At decision step 1040, when no lane is detected (e.g., indicating all lanes have been found), the process proceeds to step 1050 where the located lanes are output, e.g., data regarding the lanes and characteristics of the lanes is output.

Figure 11:
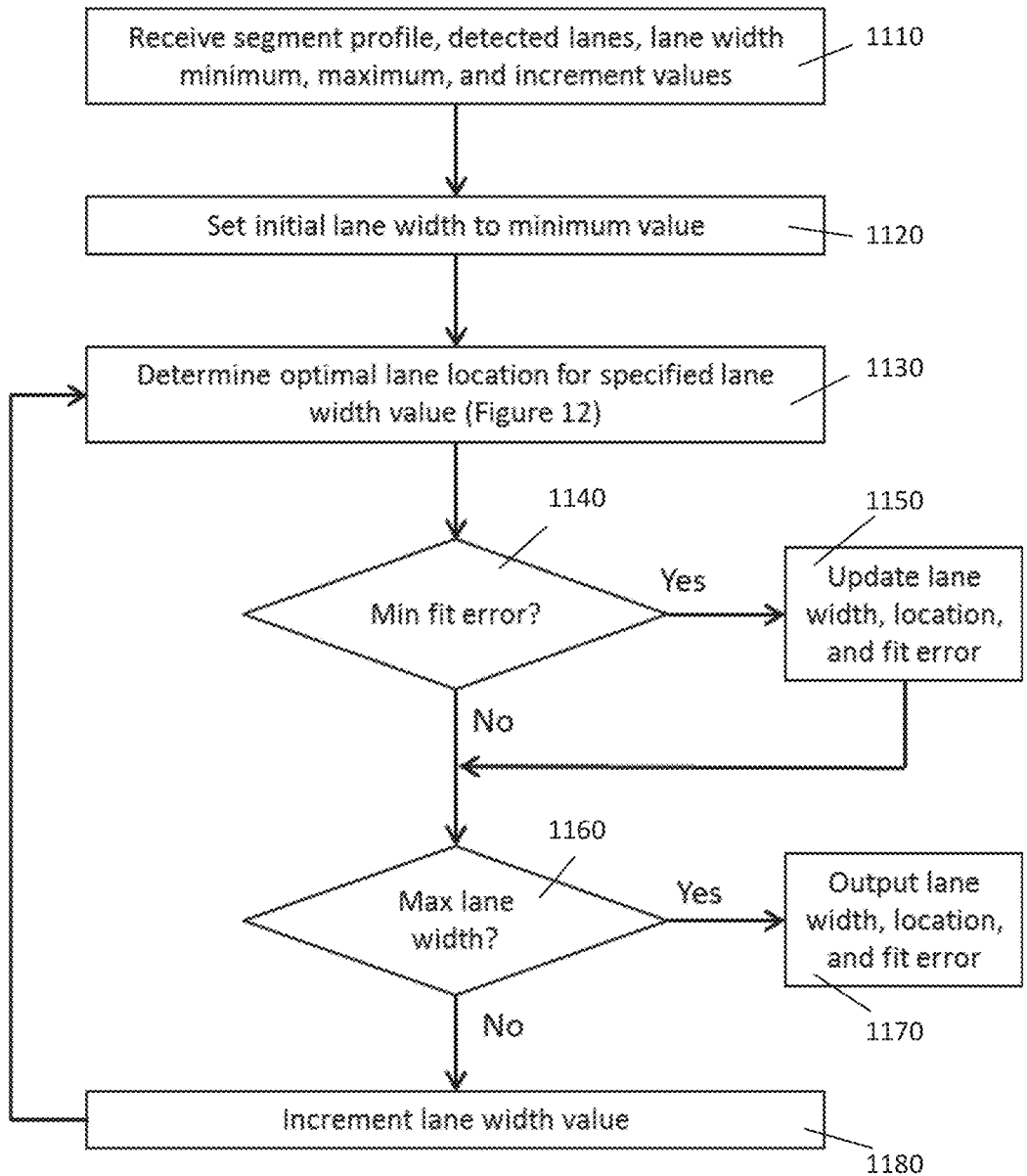
FIG. 11 is a flow diagram for a method for determining the optimal lane width and location within an image ROI segment, according to an example embodiment.

As shown in FIG. 11, a method for detecting an optimal lane width and location begins, at step 1110, where the segment profile, detected lanes and lane width minimum, maximum and incremental values are received. At step 1120, the first lane is found by setting the initial lane width value equal to the minimum value. Then the optimal lane location is determined for the specified lane width value at step 1130. An embodiment of a method for determining an optimal lane location for a specified lane width value (step 1130) is illustrated in the flow diagram FIG. 12 (discussed in more detail below). At decision step 1140, when a minimum fit error is not determined, the process moves to decision step 1160. When a minimum fit error is determined, the lane width, location and fit error is updated (step 1150) and the process proceeds to decision step 1160. At decision step 1160, if the maximum lane width value has been used, the lane width, location and fit error is output at step 1170. At decision step 1160, if the maximum lane width value has not been used, the lane width value is incremented (using the incremental value) at step 1180 and the process returns to step 1130.

Figure 12:
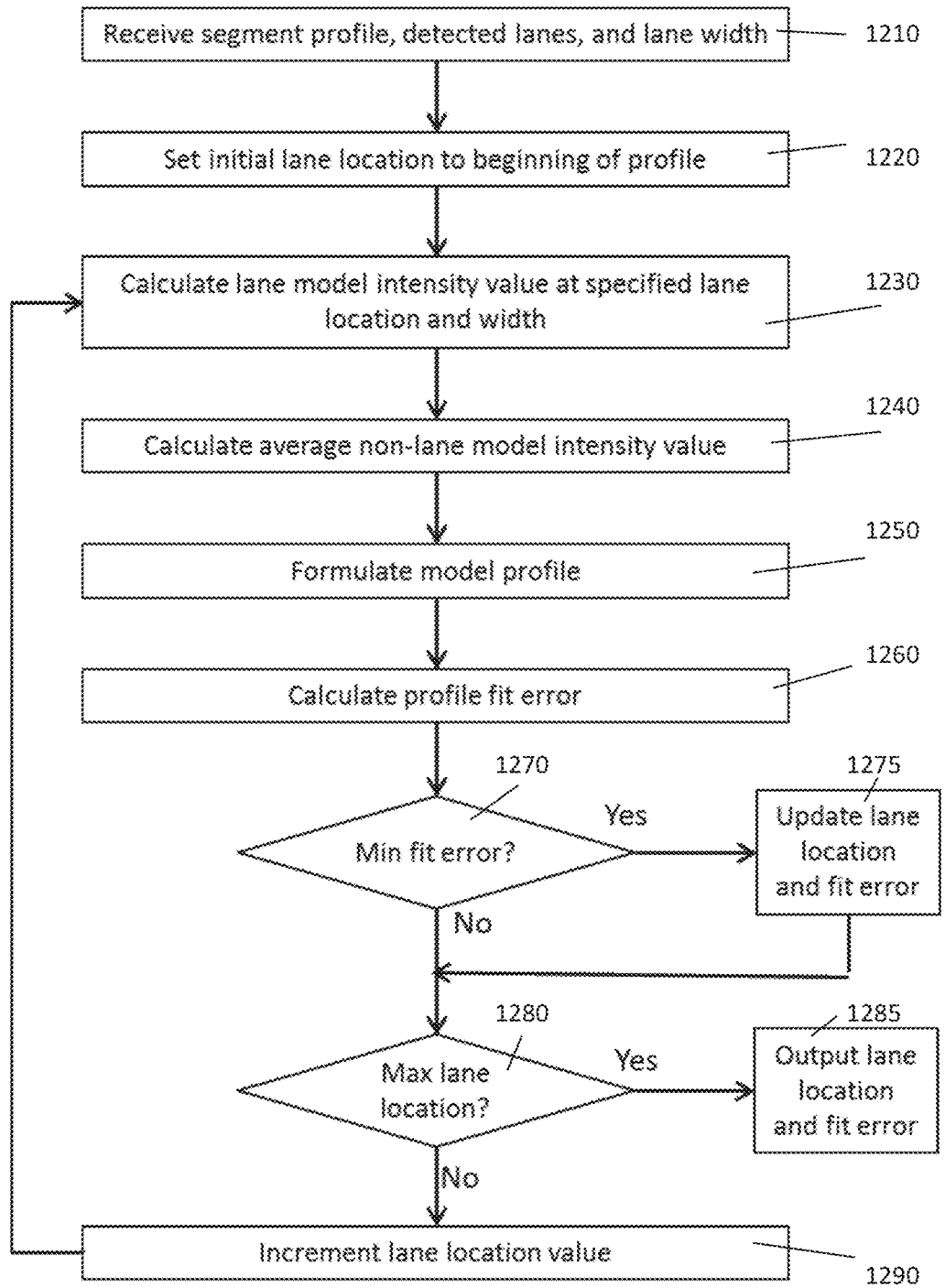
FIG. 12 is a flow diagram for a method for determining the optimal lane location for a specified lane width value within an image ROI segment, according to an example embodiment.

As shown in FIG. 12, a method for determining an optimal lane location for a specified lane width value begins, at step 1210, where the segment profile, detected lanes and lane width values are received. At step 1220, the initial lane location is set equal to the beginning of the profile. At step 1230, the lane intensity value for the model profile is calculated, e.g., by averaging the intensity values of the segment intensity profile at the specified lane location and width. At step 1240, non-lane intensity values for the model profile are calculated by averaging the intensity values of the segment intensity profile where there are no located lanes. At step 1250, the model profile is updated with the calculated lane and non-lane intensity values. Next, at step 1260, a profile fit error (profileFitErr$_i$) is calculated. In an embodiment, the profile fit error is calculated in accordance with Equation 5 as follows:

$$\text{profileFitErr}_i = \Sigma_{m=1}^{N}(\text{segProfile}_{(i,m)} - \text{modelProfile}_{(i,m)})^2 \quad (5)$$

where segProfile$_{(i,m)}$=segment profile data intensity values, modelProfile$_{(i,m)}$=model profile data intensity values, $i$=1 to $M$($M$=number of segment profiles), and $m$=1 to $N$($N$=number of segment profile data points).

At decision step 1270, when a fit error is not determined to be a minimum fit error, the process moves to decision step 1280. When a fit error is determined to be a minimum fit error, the lane location and fit error is updated (step 1275) and the process proceeds to decision step 1280. At decision step 1280, if the maximum lane location value has been used, the lane location and fit error is output at step 1285. At decision step 1280, if the maximum lane location value has not been used, the lane location value is incremented at step 1290 and the process returns to step 1230.

Figure 13:
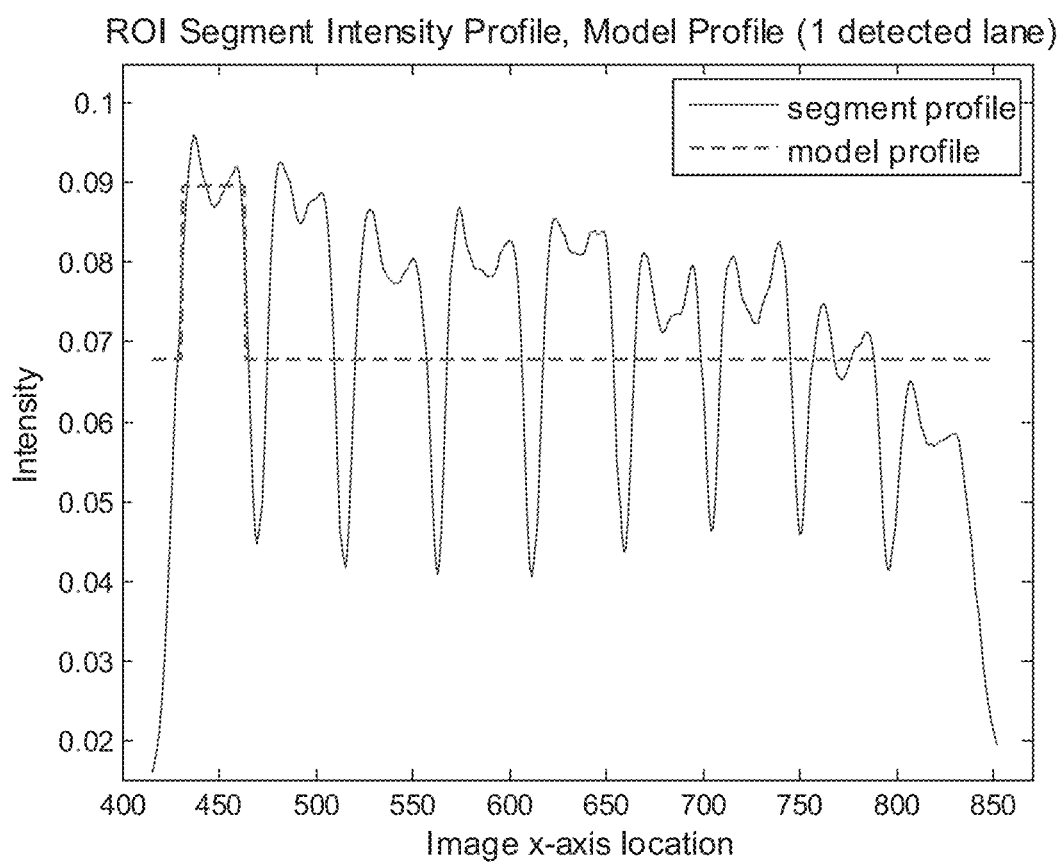
FIG. 13 is a conceptual diagram of an image ROI segment intensity profile and model profile for one detected lane, according to an example embodiment.
Figure 14:
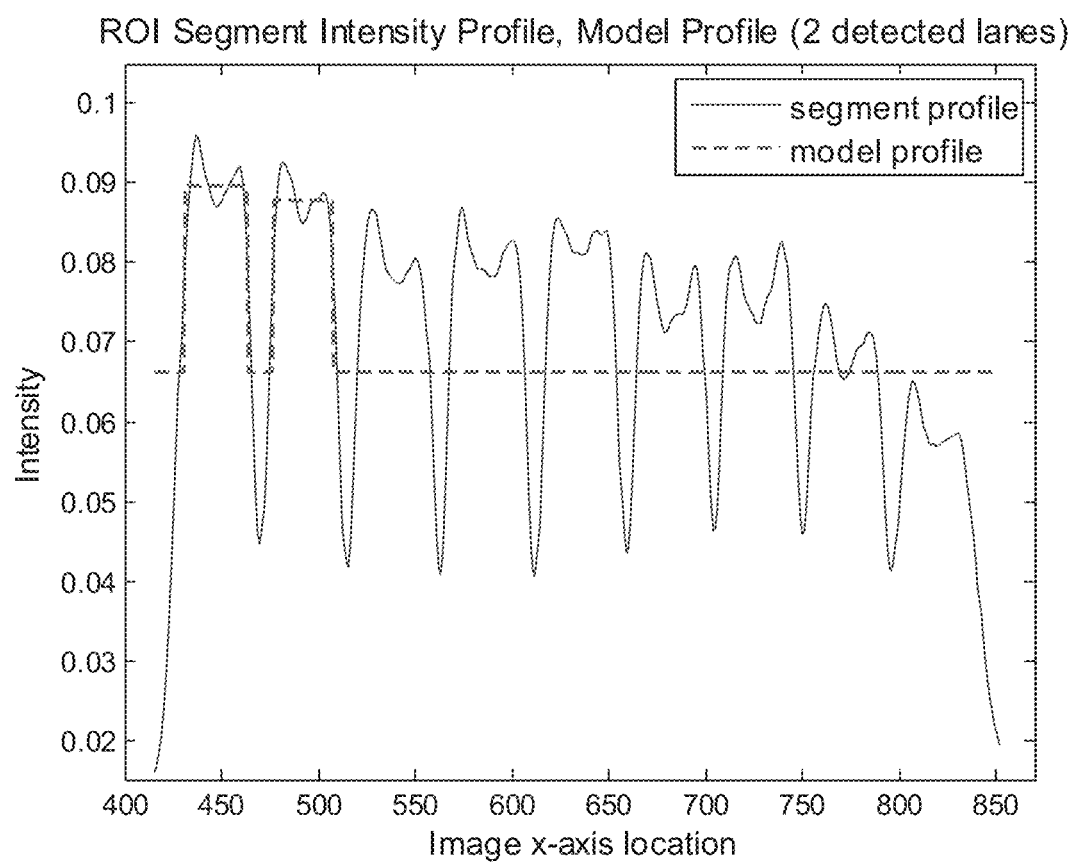
FIG. 14 is a conceptual diagram of an image ROI segment intensity profile and model profile for two detected lanes, according to an example embodiment.
Figure 15:
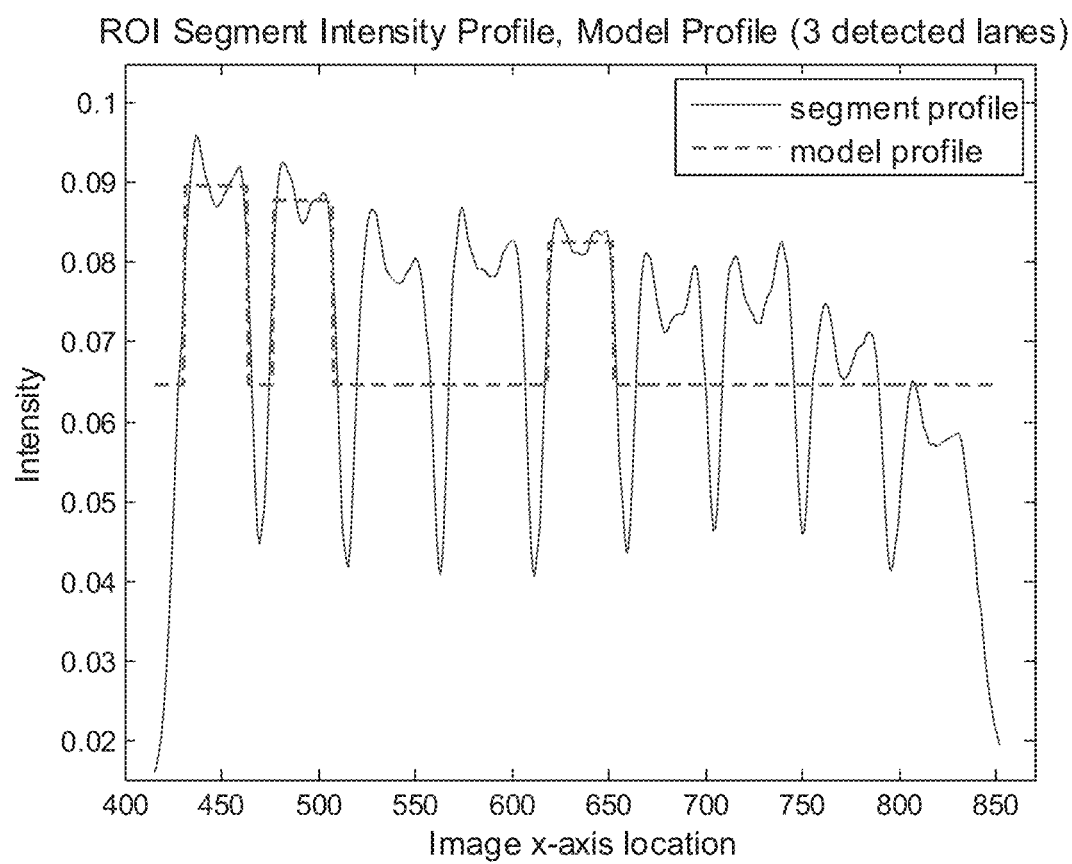
FIG. 15 is a conceptual diagram of an image ROI segment intensity profile and model profile for three detected lanes, according to an example embodiment.
Figure 16:
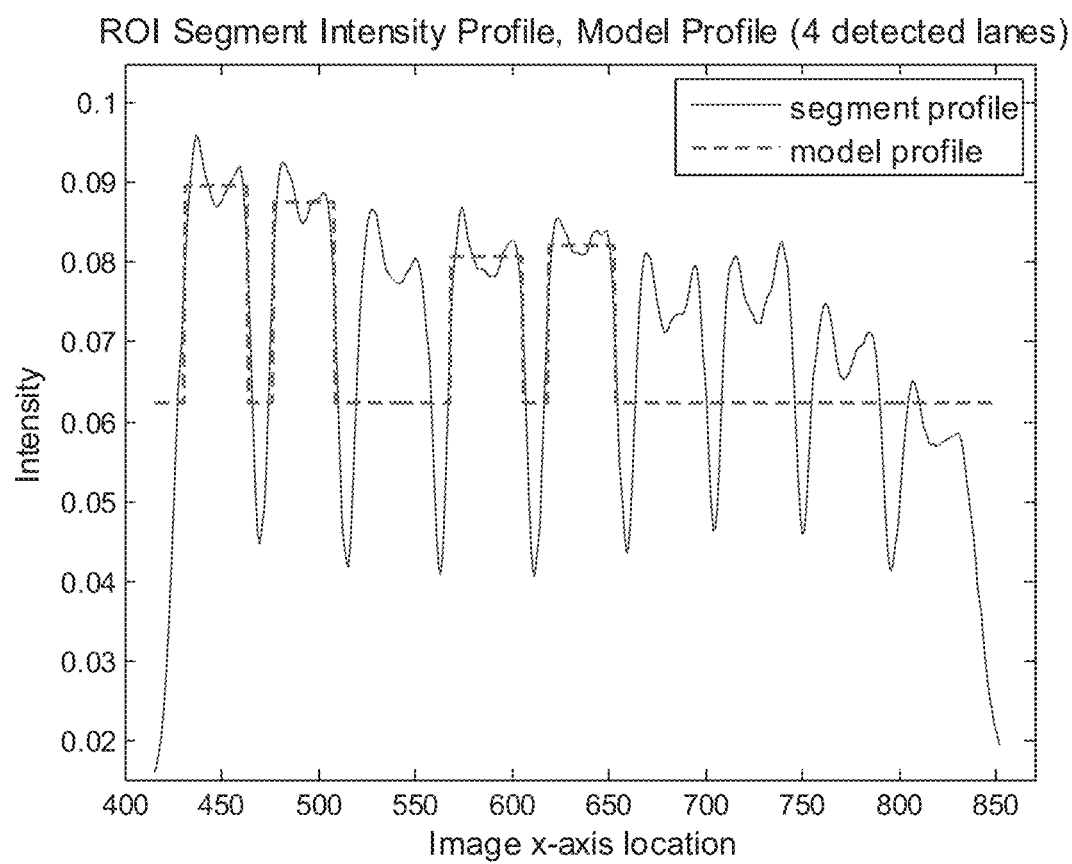
FIG. 16 is a conceptual diagram of an image ROI segment intensity profile and model profile for four detected lanes, according to an example embodiment.
Figure 17:
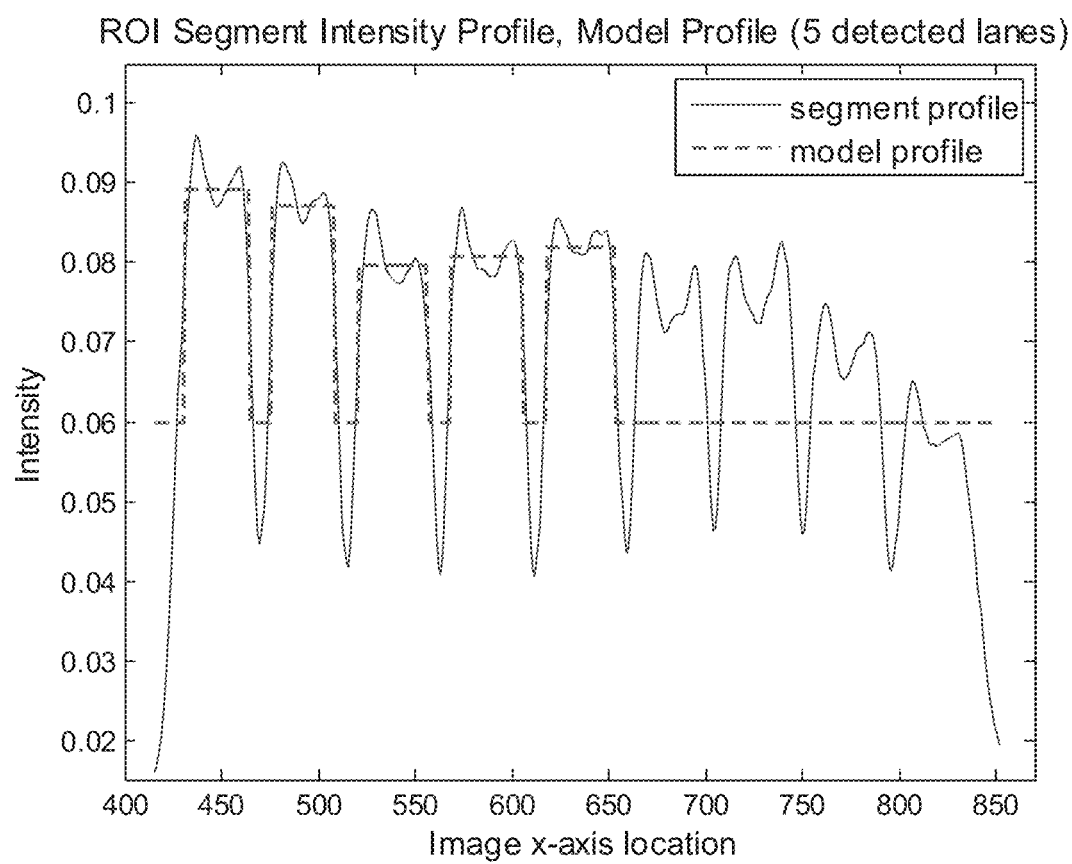
FIG. 17 is a conceptual diagram of an image ROI segment intensity profile and model profile for five detected lanes, according to an example embodiment.
Figure 18:
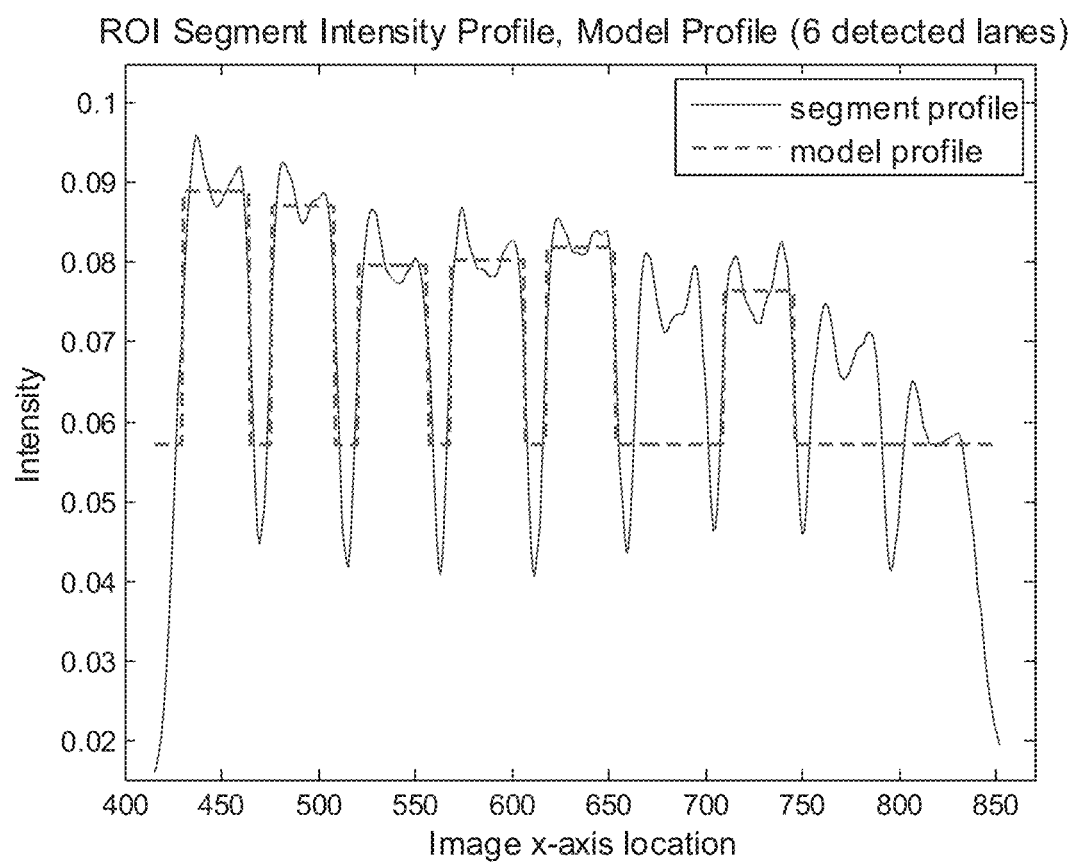
FIG. 18 is a conceptual diagram of an image ROI segment intensity profile and model profile for six detected lanes, according to an example embodiment.
Figure 19:
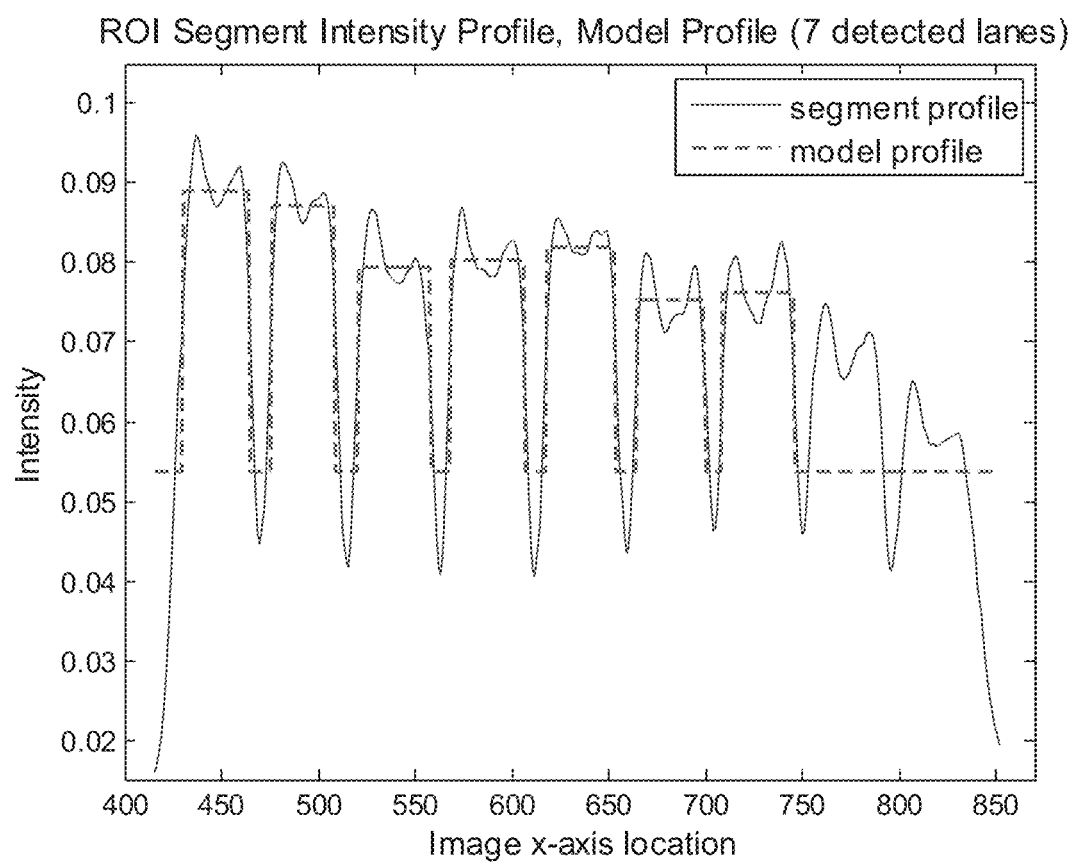
FIG. 19 is a conceptual diagram of an image ROI segment intensity profile and model profile for seven detected lanes, according to an example embodiment.
Figure 20:
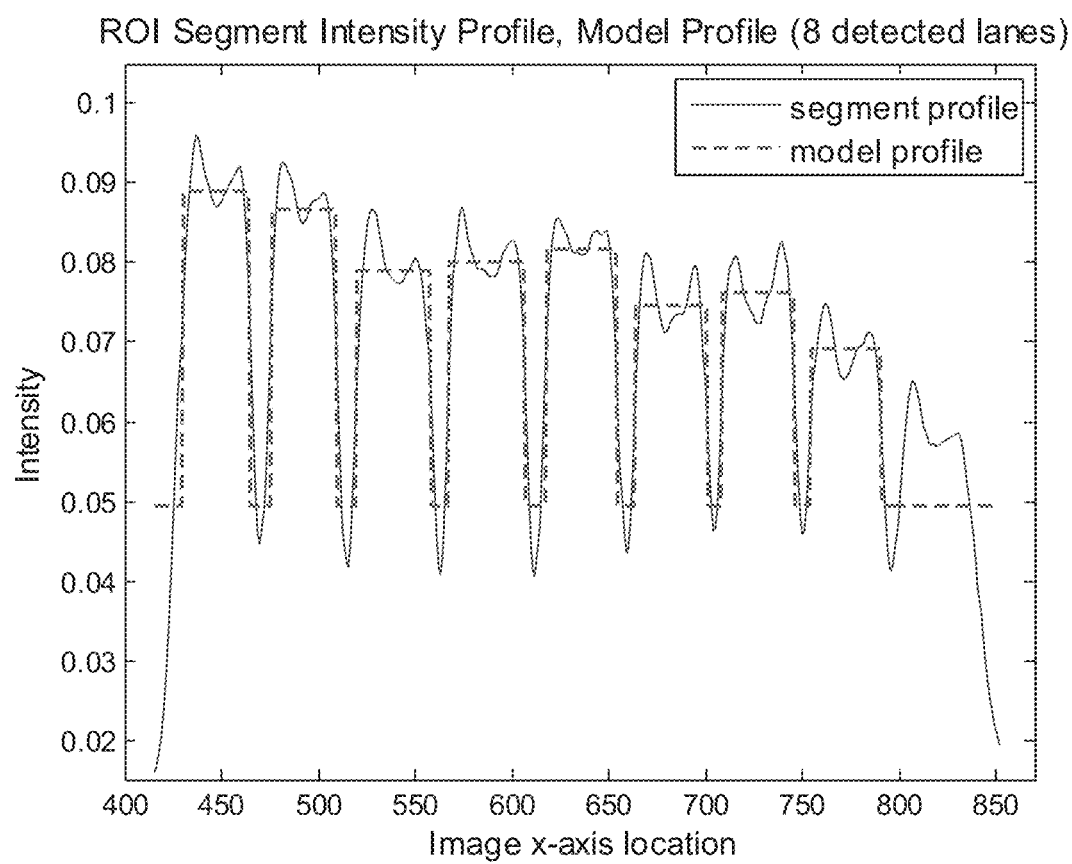
FIG. 20 is a conceptual diagram of an image ROI segment intensity profile and model profile for eight detected lanes, according to an example embodiment.
Figure 21:
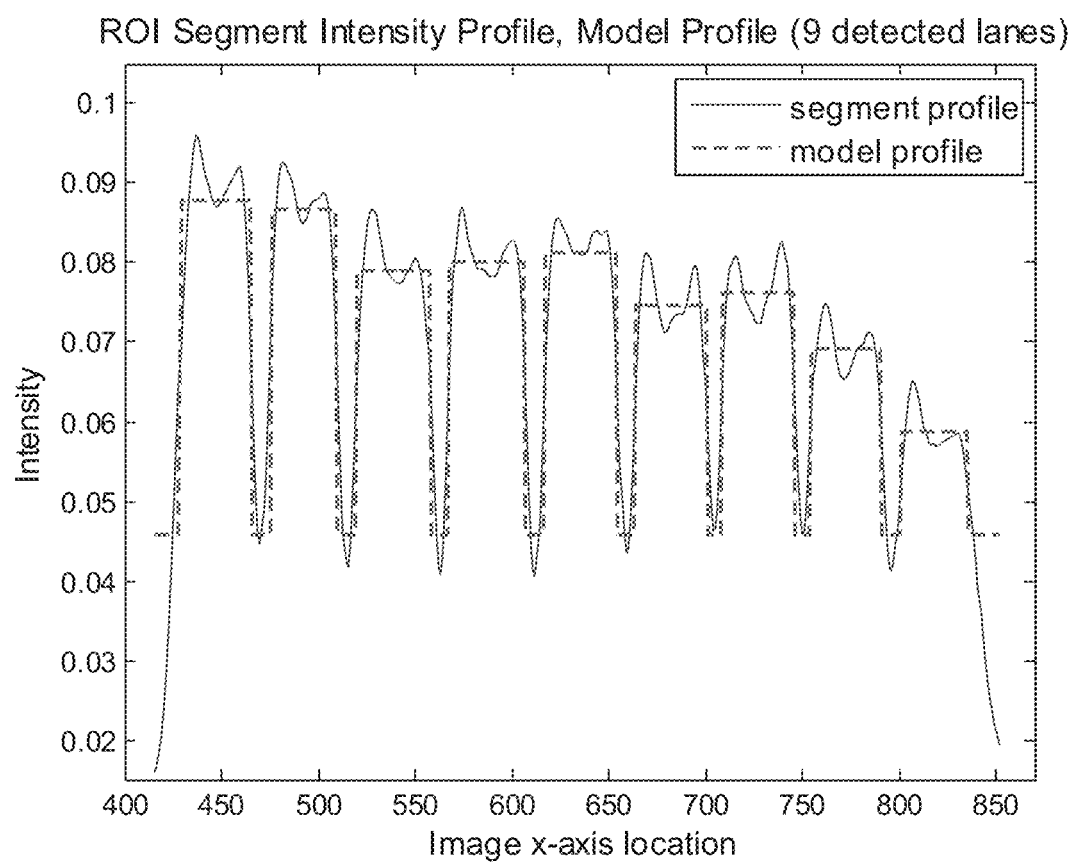
FIG. 21 is a conceptual diagram of an image ROI segment intensity profile and model profile for nine detected lanes, according to an example embodiment.

In this manner, the profile fit error is calculated for all possible lane locations and associated lane width increments. The detected lane is the lane location and associated lane width value resulting in the lowest profile fit error. The model of the segment intensity profile for the resultant detected lane is illustrated in FIG. 13. Additional lanes are detected by repeating this iterative process until all lanes are found in the ROI segment. Results of the incrementally updated detected lanes and their associated model profiles are illustrated in FIGS. 14-21.

Figure 23:
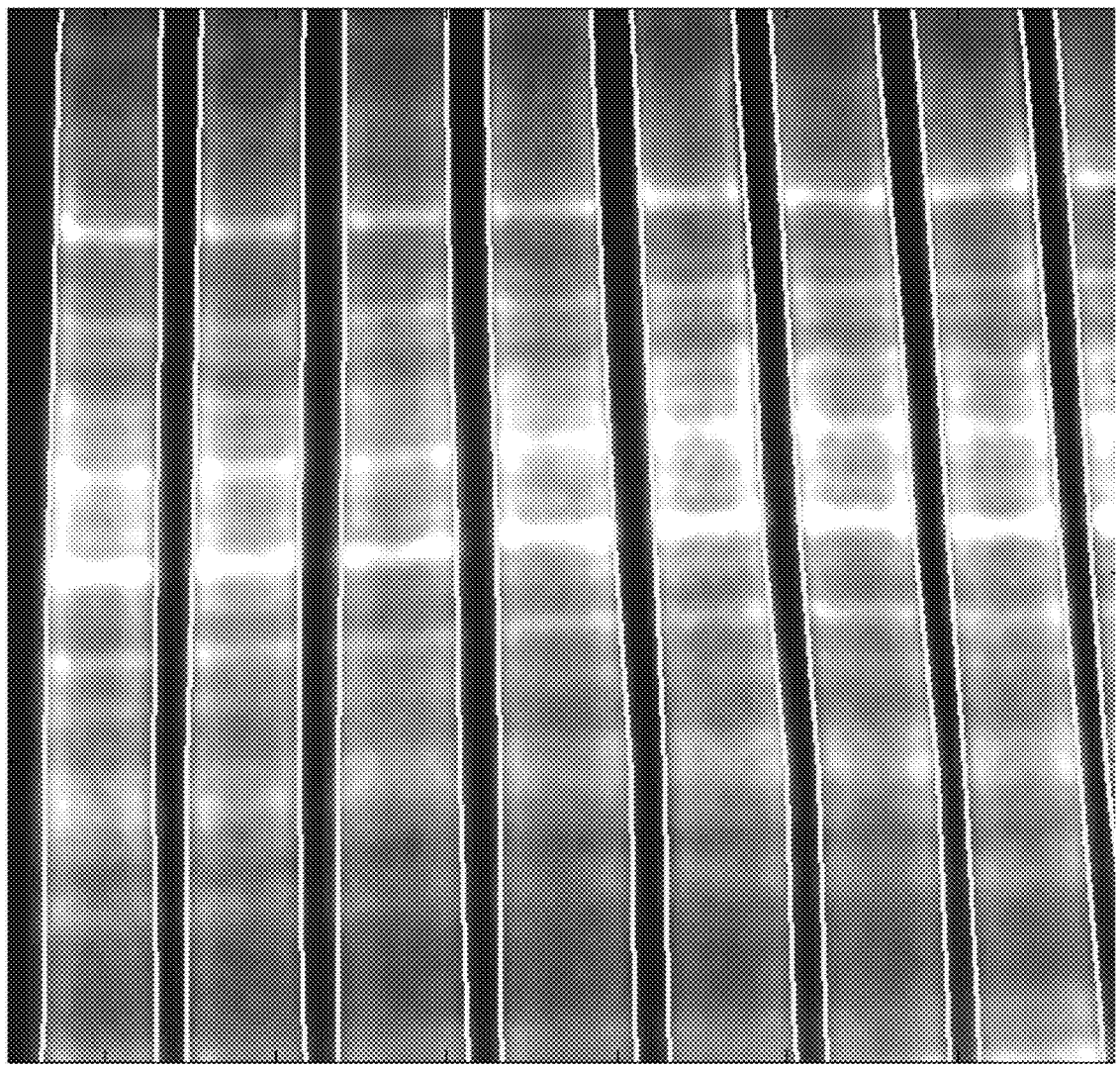
FIG. 23 is a conceptual diagram illustrating the zoomed in detected lane results of the method for an example image ROI, according to an example embodiment.
Figure 24:
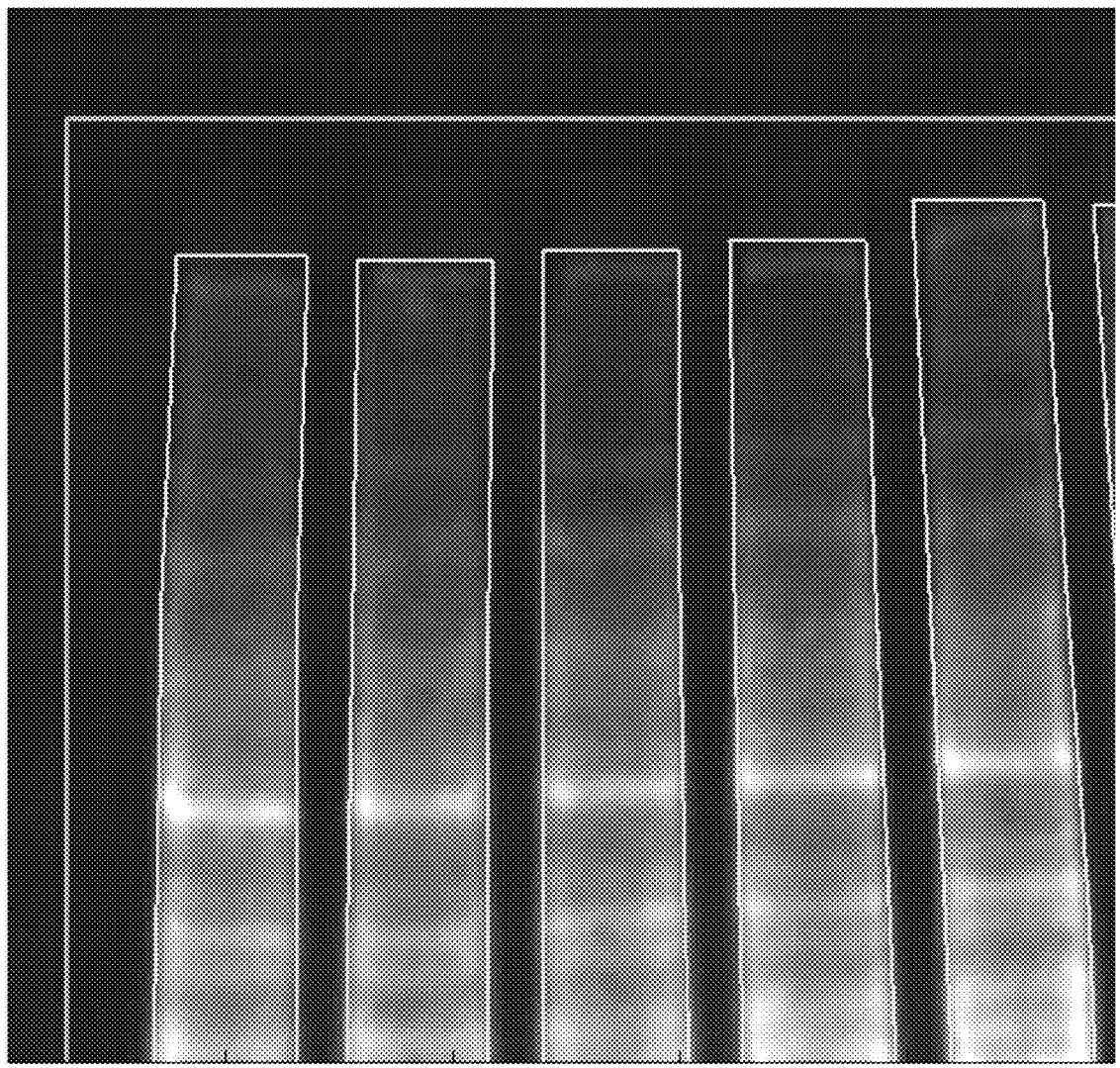
FIG. 24 is a conceptual diagram illustrating the zoomed in detected lane results of the method for an example image ROI, according to an example embodiment.

Returning to step 270 of FIG. 2, each of the identified lane locations within each ROI segment may be accurately assembled together to formulate one cohesive set of lanes in the entire ROI. The characterization of each lane across all data/ROI segments will then be complete and can be output or displayed (step 280), e.g., as illustrated in FIGS. 22-24.

Figure 25:
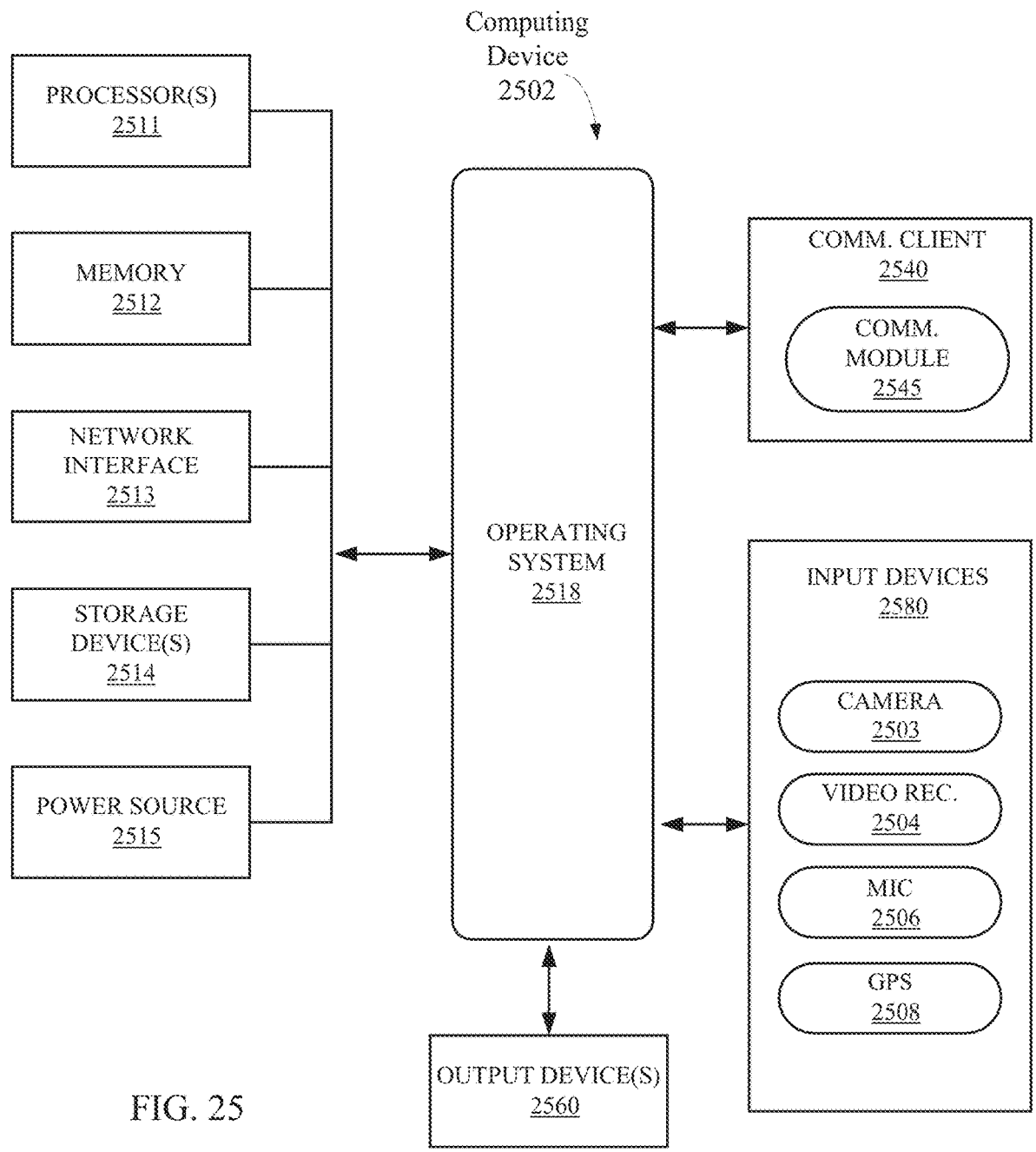
FIG. 25 is a block diagram of example functional components for a computing system or device configured to perform one or more of the analysis techniques described herein, according to an embodiment.

FIG. 25 is a block diagram of example functional components for a computing system or device 2502 configured to perform one or more of the analysis techniques described herein above and/or below, according to an embodiment. One particular example of computing device 2502 is illustrated. Many other embodiments of the computing device 2502 may be used. In the illustrated embodiment of FIG. 25, the computing device 2502 includes one or more processor(s) 2511, memory 2512, a network interface 2513, one or more storage devices 2514, a power source 2515, output device(s) 2560, and input device(s) 2580. The computing device 2502 also includes an operating system 2518 and a communications client 2540 that are executable by the computing device 2502. Each of components 2511, 2512, 2513, 2514, 2515, 2560, 2580, 2518, and 2540 is interconnected physically, communicatively, and/or operatively for inter-component communications in any operative manner.

As illustrated, processor(s) 2511 are configured to implement functionality and/or process instructions for execution within computing device 2502. For example, processor(s) 2511 execute instructions stored in memory 2512 or instructions stored on storage devices 2514. The processor may be implemented as an ASIC including an integrated instruction set. Memory 2512, which may be a non-transient computer-readable storage medium, is configured to store information within computing device 2502 during operation. In some embodiments, memory 2512 includes a temporary memory, area for information not to be maintained when the computing device 2502 is turned OFF. Examples of such temporary memory include volatile memories such as random access memories (RAM), dynamic random access memories (DRAM), and static random access memories (SRAM). Memory 2512 maintains program instructions for execution by the processor(s) 2511. Example programs can include the adaptive lane detection engine 108 in FIG. 1.

Storage devices 2514 also include one or more non-transient computer-readable storage media. Storage devices 2514 are generally configured to store larger amounts of information than memory 2512. Storage devices 2514 may further be configured for long-term storage of information. In some examples, storage devices 2514 include non-volatile storage elements. Non-limiting examples of non-volatile storage elements include magnetic hard disks, optical discs, floppy discs, flash memories, or forms of electrically programmable memories (EPROM) or electrically erasable and programmable (EEPROM) memories.

The computing device 2502 uses network interface 2513 to communicate with external devices via one or more networks. Network interface 2513 may be a network interface card, such as an Ethernet card, an optical transceiver, a radio frequency transceiver, or any other type of device that can send and receive information. Other non-limiting examples of network interfaces include wireless network interface, Bluetooth®, 9G and WiFi® radios in mobile computing devices, and USB (Universal Serial Bus). In some embodiments, the computing device 2502 uses network interface 2513 to wirelessly communicate with an external device or other networked computing device.

The computing device 2502 includes one or more separate or integrated input devices 2580. Some input devices 2580 are configured to sense the environment and capture images or other signals. Some input devices 2580 are configured to receive input from a user through tactile, audio, video, or other sensing feedback. Non-limiting examples of input devices 2580 include a presence-sensitive screen, a mouse, a keyboard, a voice responsive system, camera 2503, a video recorder 2504, a microphone 2506, a GPS module 2508, or any other type of device for detecting a command from a user or for sensing the environment. In some examples, a presence-sensitive screen includes a touch-sensitive screen.

One or more output devices 2560 are also included in computing device 2502. Output devices 2560 are configured to provide output to another system or device or to a user using tactile, audio, and/or video stimuli. Output devices 2560 may include a display screen (e.g., a separate screen or part of the presence-sensitive screen), a sound card, a video graphics adapter card, or any other type of device for converting a signal into an appropriate form understandable to humans or machines. Additional examples of output device 2560 include a speaker, a cathode ray tube (CRT) monitor, a liquid crystal display (LCD), or any other type of device that can generate intelligible output to a user. In some embodiments, a device may act as both an input device and an output device.

The computing device 2502 includes one or more power sources 2515 to provide power to the computing device 2502. Non-limiting examples of power source 2515 include single-use power sources, rechargeable power sources, and/or power sources developed from nickel-cadmium, lithium-ion, or other suitable material.

The computing device 2502 includes an operating system 2518. The operating system 2518 controls operations of the components of the computing device 2502. For example, the operating system 2518 facilitates the interaction of communications client 2540 with processors 2511, memory 2512, network interface 2513, storage device(s) 2514, input device 2580, output device 2560, and power source 2515.

As also illustrated in FIG. 25, the computing device 2502 includes communications client 2540. Communications client 2540 includes communications module 2545. Each of communications client 2540 and communications module 2545 includes program instructions and/or data that are executable by the computing device 2502. For example, in one embodiment, communications module 2545 includes instructions causing the communications client 2540 executing on the computing device 2502 to perform one or more of the operations and actions described in the present disclosure. In some embodiments, communications client 2540 and/or communications module 2545 form a part of operating system 2518 executing on the computing device 2502.

According to various embodiments, one or more of the components shown in FIG. 25 may be omitted from the computing device 2502.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law.

Moreover, any combination of the above-described elements in all possible variations thereof is encompassed by the disclosure unless otherwise indicated herein or otherwise clearly contradicted by context.

The invention claimed is:

1. A computer-implemented method of automatically identifying and characterizing one or more lanes in image data for one or more electrophoresed samples, the method comprising:
   receiving image data representing an image of one or more lanes of electrophoresed samples;
   segmenting the image data into one or multiple data segments within a region of interest (ROI) in the image, along a first axis in the ROI, each of the one or multiple data segments traversing one or multiple lanes of the one or more lanes;
   generating an intensity profile for at least a first data segment of the one or multiple data segments along a second axis orthogonal to the first axis in the ROI;
   determining an approximate lane width value for the one or multiple lanes, by:
      calculating a derivative of the intensity profile across the second axis to produce a differential curve, the differential curve including positive and negative differential curve pairs;
      iteratively producing an array of shifted differential curves by: incrementally shifting the positive and negative differential curve pairs relative to each other by incremental amounts defined by a minimum and a maximum lane width shift parameter value; and combining the positive and negative differential curve pairs together for each lane width shift parameter value to produce a shifted differential curve;
      for each of the shifted differential curves in the array: squaring or taking the absolute value and combining the differential curve, and determining a lane width fit error; and
      determining a minimum lane width fit error, wherein the lane width shift parameter value corresponding to the minimum lane width fit error is determined as the approximate lane width value;
   processing the intensity profile and the approximate lane width value for the one or multiple lanes to determine a location and parameters for each of the one or multiple lanes represented in the first data segment; and
   outputting the determined locations and parameters of the one or multiple lanes represented in the first data segment.

2. The method of claim 1, further including receiving a selection of the ROI, the ROI including data representing the one or multiple lanes.

3. The method of claim 2, wherein the selection of the ROI includes a selection received from a user input device.

4. The method of claim 2, wherein the selection of the ROI includes a selection received from, or identified by, an artificial intelligence algorithm.

5. The method of claim 1, wherein the parameters include the approximate lane width value for the one or multiple lanes.

6. The method of claim 1, further including detecting the one or multiple lanes in the first data segment based on the determined approximate lane width value.

7. The method of claim 1, further comprising rendering an image of the one or multiple lanes in the first data segment in the ROI, and/or an outline of the one or multiple lanes in the first data segment in the ROI based on the determined locations and parameters of the one or multiple lanes in the first data segment.

8. The method of claim 1, wherein the generating the intensity profile includes summing up intensity values in the first data segment along the first axis for each of a plurality of second axis locations.

9. A computer-implemented method of automatically identifying and characterizing one or more lanes in image data for one or more electrophoresed samples, the method comprising:
   receiving image data representing an image of one or more lanes of electrophoresed samples;
   segmenting the image data into one or multiple data segments within a region of interest (ROI) in the image, along a first axis in the ROI, each of the one or multiple data segments traversing one or multiple lanes of the one or more lanes;
   generating an intensity profile for at least a first data segment of the one or multiple data segments along a second axis orthogonal to the first axis in the ROI;
   determining an approximate lane width value for the one or multiple lanes;
   processing the intensity profile and the approximate lane width value for the one or multiple lanes to determine a location and parameters for each of the one or multiple lanes represented in the first data segment; and
   outputting the determined locations and parameters of the one or multiple lanes represented in the first data segment; and
   detecting the one or multiple lanes in the first data segment based on the determined approximate lane width value, by:
      determining a minimum lane width value, a maximum lane width value and an increment value based on the approximate lane width value; and
      detecting an optimal lane width and locations for each of the one or multiple lanes using an iterative lane width and location determination algorithm, wherein for each incremental value starting with the maximum or minimum lane width value, a model profile is determined and compared with the intensity profile.

10. A computer-implemented method of automatically identifying and characterizing one or more lanes in image data for one or more electrophoresed samples, the method comprising:
   receiving image data representing an image of one or more electrophoresed samples;
   segmenting the image data into two or multiple data segments within a region of interest (ROI) in the image, along a first axis in the ROI, each of the two or multiple data segments traversing one or multiple lanes;
   generating an intensity profile for each of the two or multiple data segments along a second axis orthogonal to the first axis in the ROI;
   processing each intensity profile to determine a location and parameters for each corresponding segment of the one or multiple data segments, wherein the parameters include an approximate lane width value, and wherein the processing includes determining the approximate lane width value for the one or multiple lanes by:
      calculating a derivative of the intensity profile across the second axis to produce a differential curve, the differential curve including positive and negative differential curve pairs;

iteratively producing an array of shifted differential curves by: incrementally shifting the positive and negative differential curve pairs relative to each other by incremental amounts defined by a minimum and a maximum lane width shift parameter value; and combining the positive and negative differential curve pairs together for each lane width shift parameter value to produce a shifted differential curve;

for each of the shifted differential curves in the array: squaring or taking the absolute value and combining the differential curve, and determining a lane width fit error; and determining a minimum lane width fit error, wherein the lane width shift parameter value corresponding to the minimum lane width fit error is determined as the approximate lane width value; and outputting the determined locations and parameters of the one or multiple lanes for each of the two or multiple data segments.

11. The method of claim 10, further comprising, for each of the one or multiple lanes in the two or multiple data segments, rendering an image of the one or multiple lanes and/or an outline of the one or multiple lanes in the two or multiple data segments based on the determined locations and parameters of the one or multiple lanes in the two or multiple data segments.

12. The method of claim 10, further comprising, for each of the one or multiple lanes, combining together the corresponding locations and parameters determined for each of the two or multiple data segments.

13. The method of claim 10, further including receiving a selection of the ROI, the ROI including data representing the one or multiple lanes.

14. The method of claim 13, wherein the selection of the ROI includes a selection received from a user input device.

15. The method of claim 13, wherein the selection of the ROI includes a selection received from, or identified by, an artificial intelligence algorithm.

16. The method of claim 10, further including detecting the one or multiple lanes in the two or multiple data segments based on the determined approximate lane width value.

17. The method of claim 16, wherein the detecting the one or multiple lanes in the two or multiple data segments includes:

determining a minimum lane width value, a maximum lane width value and an increment value based on the approximate lane width value; and detecting an optimal lane width and locations for each of the one or more lanes using an iterative lane width and location determination algorithm, wherein for each incremental value starting with the maximum or minimum lane width value, a model profile is determined and compared with the intensity profile in the two or multiple data segments.

18. The method of claim 10, wherein the generating the intensity profile includes summing up intensity values in the two or multiple data segments along the second axis for each of a plurality of first axis locations.

19. A system configured to automatically identify and characterize one or more lanes in image data for one or more electrophoresed samples, the system comprising:

one or more processors; and a memory storing instructions, which when executed by the one or more processors, cause the one or more processors to:

receive image data representing an image of one or more lanes of electrophoresed samples;

segment the image data into one or multiple data segments within a region of interest (ROI) in the image, along a first axis in the ROI, each of the one or multiple data segments traversing one or multiple lanes of the one or more lanes;

generate an intensity profile for at least a first data segment of the one or multiple data segments along a second axis orthogonal to the first axis in the ROI;

determine an approximate lane width value for the one or multiple lanes, by:

calculating a derivative of the intensity profile across the second axis to produce a differential curve, the differential curve including positive and negative differential curve pairs;

iteratively producing an array of shifted differential curves by: incrementally shifting the positive and negative differential curve pairs relative to each other by incremental amounts defined by a minimum and a maximum lane width shift parameter value; and combining the positive and negative differential curve pairs together for each lane width shift parameter value to produce a shifted differential curve;

for each of the shifted differential curves in the array: squaring or taking the absolute value and combining the differential curve, and determining a lane width fit error; and determining a minimum lane width fit error, wherein the lane width shift parameter value corresponding to the minimum lane width fit error is determined as the approximate lane width value;

process the intensity profile and the approximate lane width value for the one or multiple lanes to determine a location and parameters for each of the one or multiple lanes in the first data segment; and output the determined locations and parameters of the one or multiple lanes in the first data segment.

20. The system of claim 19, wherein the instructions, when executed by the one or more processors, further cause the one or more processors to detect the one or multiple lanes in the first data segment based on the determined approximate lane width value, by:

determining a minimum lane width value, a maximum lane width value and an increment value based on the approximate lane width value; and detecting an optimal lane width and locations for each of the one or multiple lanes using an iterative lane width and location determination algorithm, wherein for each incremental value starting with the maximum or minimum lane width value, a model profile is determined and compared with the intensity profile.

21. A system configured to automatically identify and characterize one or more lanes in image data for one or more electrophoresed samples, the system comprising:

one or more processors; and a memory storing instructions, which when executed by the one or more processors, cause the one or more processors to perform the steps of:

receiving image data representing an image of one or more electrophoresed samples;

segmenting the image data into two or multiple data segments within a region of interest (ROI) in the image, along a first axis in the ROI, each of the two or multiple data segments traversing one or multiple lanes;

generating an intensity profile for each of the two or multiple data segments along a second axis orthogonal to the first axis in the ROI;

processing each intensity profile to determine a location and parameters for each corresponding segment of the two or multiple data segments, wherein the parameters include an approximate lane width value, and wherein the processing includes determining the approximate lane width value for the one or multiple lanes by:

calculating a derivative of the intensity profile across the second axis to produce a differential curve, the differential curve including positive and negative differential curve pairs;

iteratively producing an array of shifted differential curves by: incrementally shifting the positive and negative differential curve pairs relative to each other by incremental amounts defined by a minimum and a maximum lane width shift parameter value; and combining the positive and negative differential curve pairs together for each lane width shift parameter value to produce a shifted differential curve;

for each of the shifted differential curves in the array: squaring or taking the absolute value and combining the differential curve, and determining a lane width fit error; and determining a minimum lane width fit error, wherein the lane width shift parameter value corresponding to the minimum lane width fit error is determined as the approximate lane width value; and outputting the determined locations and parameters of the one or multiple lanes for each of the two or multiple data segments.

22. The system of claim 21, wherein the instructions, when executed by the one or more processors, further cause the one or more processors to detect the one or multiple lanes in the two or multiple data segments by:

determining a minimum lane width value, a maximum lane width value and an increment value based on the approximate lane width value; and detecting an optimal lane width and locations for each of the one or more lanes using an iterative lane width and location determination algorithm, wherein for each incremental value starting with the maximum or minimum lane width value, a model profile is determined and compared with the intensity profile in the two or multiple data segments.

* * * * *